US009222125B2

(12) United States Patent
Zhang

(10) Patent No.: US 9,222,125 B2
(45) Date of Patent: Dec. 29, 2015

(54) DIMERIC DIAGNOSTIC ARRAYS

(75) Inventor: Ning Zhang, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/448,087

(22) Filed: Apr. 16, 2012

(65) Prior Publication Data
US 2013/0023445 A1 Jan. 24, 2013

Related U.S. Application Data

(60) Provisional application No. 61/476,143, filed on Apr. 15, 2011.

(51) Int. Cl.
C12M 1/34 (2006.01)
C12M 3/00 (2006.01)
C12Q 1/68 (2006.01)
C12P 19/34 (2006.01)
C07H 21/02 (2006.01)
C07H 21/04 (2006.01)

(52) U.S. Cl.
CPC ............. *C12Q 1/6837* (2013.01); *C12Q 1/689* (2013.01); *C12Q 1/6895* (2013.01)

(58) Field of Classification Search
USPC .................. 435/6.1, 6.11, 91.1, 283.1, 287.1, 435/287.2; 436/94, 501; 536/23.1, 24.3, 536/24.33
See application file for complete search history.

(56) References Cited

U.S. PATENT DOCUMENTS

2006/0183120 A1* 8/2006 Teh et al. ........................ 435/6

OTHER PUBLICATIONS

Liang et al., An oligonucleotide microarray for microRNA expression analysis based on labeling RNA with quantum dot and nanogold probe. Nucleic Acids Research, 33 (2), e17, 2005.*
Abdullahi et al., "Microarray immunoassay for the detection of grapevine and tree fruit viruses", *J. Virol. Methods* 160, 90-100 (2009).
Barad et al., "MicroRNA expression detected by oligonucleotide microarrays: System establishment and expression profiling in human tissues", *Genome Res.* 14, 2486-2494 (2004).
Chatterjee et al., "Diagnostic Markers of Ovarian Cancer by High-Throughput Antigen Cloning and Detection on Arrays", *Cancer Res.* 66(2), 1181-1190 (2006).
Chou et al., "Optimization of probe length and the number of probes per gene for optimal microarray analysis of gene expression", *Nucleic Acids Res.* 32 (12), e99, 8 pages (2004).
Dadoune et al., "Identification of transcripts by macroarrays, RT-PCR and in situ hybridization in human ejaculate spermatozoa", *Mol. Hum. Reprod.* 11(2), 133-140 (2005).

Fessehaie et al., "An Oligonucleotide Array for the Identification and Differentiation of Bacteria Pathogenic on Potato", *Phytopathology* 93 (3), 262-269 (2003).
Gilbert et al., "Plant Pathology and Nematology, Development of a DNA-based Macroarray for the Detection and Identification of *Fusarium oxysporum* f. sp. *vasinfectum* in Cotton Tissue", *J. Cotton Science* 12, 165-170 (2008).
Goff et al., "Rational Probe Optimization and Enhanced Detection Strategy for MicroRNAs Using Microarrays", *RNA Biology* 2(3), 93-100 (2005).
Guo et al., "Enhanced discrimination of single nucleotide polymorphisms by artificial mismatch hybridization", *Nat. Biotechnol.* 15, 331-335 (1997).
Ivnitski et al., "Nucleic acid approaches for detection and identification of biological warfare and infectious disease agents", *Biotechniques* 35, 862-869 (2003).
Lee et al., "Detection of bacterial pathogens in municipal wastewater using an oligonucleotide microarray and real-time quantitative PCR", *J. Microbiol. Meth.* 65, 453-467 (2006).
Li et al., "Selection of optimal DNA oligos for gen expression arrays", *Bioinformatics* 17(11), 1067-1076 (2001).
Lievens et al., "Design and development of a DNA array for rapid detection and identification of multiple tomato vascular wilt pathogens", *FEMS Microbiol, Lett.,* 223, 113-122 (2003).
Lievens et al., "Quantitative assessment of phytopathogenic fungi in various substrates using a DNA macroarray", *Environ. Microbiol.* 7 (11), 1698-1710 (2005).
Lievens et al., "Recent Developments in Pathogen Detection Arrays: Implications for Fungal Plant Patnogens and Use in Practice", *Phytopathology* 95 (12), 1374-1380 (2005).
Lievens et al., "From extensive clone libraries to comprehensive DNA arrays efficient and simultaneous detection and identification of orchid mycorrhizal fungi", *J. Microbiol. Meth.* 80, 76-85 (2010).
Loy et al., "Highly parallel microbial diagnostics using oligonucleotide microarrays", *Clin. Chim. Acta* 363, 106-119 (2006).
Maoka et al., "Application of cDNA Macroarray for Simultaneou Detection of 12 Potato Viruses", *Plant Dis.* 94 (10), 1248-1254 (2010).
Njambere et al., "Macroarray Detection of Fungal Turfgrass Pathogens", Presentation at American Phytopathelogical Meeting, Charlotte, NC, 18 pages (Aug. 2010).
Njambere et al., "Dimeric oligonucleotide probes enhance diagnostic macroarray performance", *Journal of Microbiological Methods,* vol. 86, 52-61 (2011).
Saiki et al., "Genetic analysis of amplified DNA with immobilized sequence-specific oligonucleotide probes", *Proc. Natl. Acad. Sci.,* 86, 6230-6234 (1989).
Shchepinov et al., "Steric factors influencing hybridization of nucleic acids to oligonucleotide arrays", *Nucleic Acids Res.* 25 (6), 1155-1161 (1997).
Sholberg et al., "Development of a DNA Macroarray for Detection and Monitoring of Economically Important Apple Diseases", *Plant Dis.* 89 (11), 1143-1150 (2005).
Southern et al., "Molecular interactions on microarrays" *Nature Genet.* 21, 5-9 (1999).
Uttamchandani et al., "Applications of microarrays in pathogen detection and biodefence", *Trends Biotechnol.* 27, 53-61 (2008).
Van Doorn et al., "Robust Detection and Identification of Multiple Oomycetes and Fungi in Environmental Samples by Using a Novel Cleavable Padlock Probe-Based Ligation Detection Assay", *Appl. Environ. Microbiol.,* 75 (12), 4185-4193 (2009).

(Continued)

*Primary Examiner* — Frank Lu
(74) *Attorney, Agent, or Firm* — Viksnins Harris & Padys PLLP

(57) ABSTRACT

The invention provides dimeric diagnostic arrays and methods for their use.

16 Claims, 5 Drawing Sheets

(56) References Cited

OTHER PUBLICATIONS

White et al., "Amplification and Direct Sequencing of Fungal Ribosomal RNA Genes for Phylogenetics", *PCR Protocols: A Guide to Methods and Applications*, Academic Press, New York, 315-322 (1990).

Wolfel et al., "Low-Density Macroarray for Rapid Detection and Identifcation of Crimean-Congo Hemorrhagic Fever Virus", *J. Clin. Microbiol.* 47 (4), 1025-1030 (2009).

Wong et al., "Optimization and clinical validation of a pathogen detection microarray", *Genome Biol.* 8, R93-R93.13 (2007).

Zhang et al., "Macroarray Detection of Solanaceous Plant Pathogens in the *Fusarium solani* Species Complex", *Plant Dis.* 91 (12), 1612-1620 (2007).

Zhang et al., "A Macroarray System for the Detection of Fungal and Oomycete Pathogens of Solanaceous Crops", *Plant Dis.* 92 (6), 953-960 (2008).

* cited by examiner

SEQUENCE LISTING

```
<160> NUMBER OF SEQ ID NOS: 308

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
ggagagagat ggcagaatgt gag                                              23

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
gggagagaga tggcagaatg tgag                                             24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
```

-continued

```
<400> SEQUENCE: 3
gaggtgtacc tgaattgtgt gagg                                               24

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
ggagagagat ggcagaatgt gagggagaga gatggcagaa tgtgag                        46

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
gggagagaga tggcagaatg tgaggggaga gagatggcag aatgtgag                      48

<210> SEQ ID NO 6
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
gaggtgtacc tgaattgtgt gagggaggtg tacctgaatt gtgtgagg                      48

<210> SEQ ID NO 7
<211> LENGTH: 56
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
ggagagagat ggcagaatgt gagaaaaaaa aaaggagaga gatggcagaa tgtgag             56

<210> SEQ ID NO 8
<211> LENGTH: 58
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
gggagagaga tggcagaatg tgagaaaaaa aaaagggaga gagatggcag aatgtgag           58

<210> SEQ ID NO 9
<211> LENGTH: 58
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 9
gaggtgtacc tgaattgtgt gaggaaaaaa aaagaggtg tacctgaatt gtgtgagg         58

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
ggagagagat ggcagaatgt gagaaaaaaa aaa                                   33

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
gggagagaga tggcagaatg tgagaaaaaa aaaa                                  34

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
gaggtgtacc tgaattgtgt gaggaaaaaa aaaa                                  34

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
ggagagagat ggcagaatgt gagaaaaaaa aaaaaaaaaa aaa                        43

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
gggagagaga tggcagaatg tgagaaaaaa aaaaaaaaaa aaaa                       44

<210> SEQ ID NO 15
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
```
gaggtgtacc tgaattgtgt gaggaaaaaa aaaaaaaaaa aaaa         44

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
cagtgttatg cttggttcca ctc         23

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
tgttgaaact tagtattaga tgcgt         25

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
gagtggaacc aagcataaca ctg         23

<210> SEQ ID NO 19
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
cagtgttatg cttggttcca ctccagtgtt atgcttggtt ccactc         46

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
tgttgaaact tagtattaga tgcgttgttg aaacttagta ttagatgcgt         50

<210> SEQ ID NO 21
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
gagtggaacc aagcataaca ctggagtgga accaagcata acactg           46

<210> SEQ ID NO 22
<211> LENGTH: 56
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
cagtgttatg cttggttcca ctcaaaaaaa aaacagtgtt atgcttggtt ccactc    56

<210> SEQ ID NO 23
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
tgttgaaact tagtattaga tgcgtaaaaa aaaaatgttg aaacttagta ttagatgcgt    60

<210> SEQ ID NO 24
<211> LENGTH: 56
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
gagtggaacc aagcataaca ctgaaaaaaa aaagagtgga accaagcata acactg    56

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
tcgcgtagta gctaacaccct cgc                                         23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
cctgtgaaca tacctaaacg ttg                                          23

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
ttatacaact catcaaccct gtga                                         24

<210> SEQ ID NO 28
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
tcgcgtagta gctaacacct cgctcgcgta gtagctaaca cctcgc                46

<210> SEQ ID NO 29
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
cctgtgaaca tacctaaacg ttgcctgtga acatacctaa acgttg                46

<210> SEQ ID NO 30
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
ttatacaact catcaaccct gtgattatac aactcatcaa ccctgtga              48

<210> SEQ ID NO 31
<211> LENGTH: 56
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
tcgcgtagta gctaacacct cgcaaaaaaa aaatcgcgta gtagctaaca cctcgc    56

<210> SEQ ID NO 32
<211> LENGTH: 56
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
cctgtgaaca tacctaaacg ttgaaaaaaa aaacctgtga acatacctaa acgttg    56

<210> SEQ ID NO 33
<211> LENGTH: 58
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
ttatacaact catcaaccct gtgaaaaaaa aaaattatac aactcatcaa ccctgtga  58

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic probe

<400> SEQUENCE: 34
tcgcgtagta gctaacacct cgcaaaaaaa aaa         33

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic probe

<400> SEQUENCE: 35
cctgtgaaca tacctaaacg ttgaaaaaaa aaa         33

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence: Synthetic probe

<400> SEQUENCE: 36
ttatacaact catcaaccct gtgaaaaaaa aaaa        34

<210> SEQ ID NO 37
<211> LENGTH: 43
<212> TYPE: DNA
<213> ORGANISM: Artificial Sequence
<220> FEATURE:
<223> OTHER INFORMATION: Description of Artificial Sequence: Synthetic probe

<400> SEQUENCE: 37
tcgcgtagta gctaacacct cgcaaaaaaa aaaaaaaaaa aaa         43

<210> SEQ ID NO 38
<211> LENGTH: 43
<212> TYPE: DNA
<213> ORGANISM: Artificial Sequence
<220> FEATURE:
<223> OTHER INFORMATION: Description of Artificial Sequence: Synthetic probe

<400> SEQUENCE: 38
cctgtgaaca tacctaaacg ttgaaaaaaa aaaaaaaaaa aaa         43

<210> SEQ ID NO 39
<211> LENGTH: 44
<212> TYPE: DNA
<213> ORGANISM: Artificial Sequence
<220> FEATURE:
<223> OTHER INFORMATION: Description of Artificial Sequence: Synthetic probe

<400> SEQUENCE: 39
ttatacaact catcaaccct gtgaaaaaaa aaaaaaaaaa aaaa        44

```
<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
cgttcctcaa attgattggc ggtc                                             24

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
gttgggactc gcgttaattc g                                                21

<210> SEQ ID NO 42
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
cgttcctcaa attgattggc ggtccgttcc tcaaattgat tggcggtc                   48

<210> SEQ ID NO 43
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
gttgggactc gcgttaattc ggttgggact cgcgttaatt cg                         42

<210> SEQ ID NO 44
<211> LENGTH: 58
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
cgttcctcaa attgattggc ggtcaaaaaa aaaacgttcc tcaaattgat tggcggtc       58

<210> SEQ ID NO 45
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
gttgggactc gcgttaattc gaaaaaaaaa agttgggact cgcgttaatt cg              52

<210> SEQ ID NO 46
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
gctgcgttct tcatcgatgc                                                   20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
tcctccgctt attgatatgc                                                   20

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
gctgcgttct tcatcgatgc gctgcgttct tcatcgatgc                             40

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
tcctccgctt attgatatgc tcctccgctt attgatatgc                             40

<210> SEQ ID NO 50
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
gctgcgttct tcatcgatgc aaaaaaaaaa gctgcgttct tcatcgatgc                  50

<210> SEQ ID NO 51
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
tcctccgctt attgatatgc aaaaaaaaaa tcctccgctt attgatatgc                  50

<210> SEQ ID NO 52
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
gctgcgttct tcatcgatgc aaaaaaaaaa                                          30

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
tcctccgctt attgatatgc aaaaaaaaaa                                          30

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
gctgcgttct tcatcgatgc aaaaaaaaaa aaaaaaaaaa                               40

<210> SEQ ID NO 55
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
tcctccgctt attgatatgc aaaaaaaaaa aaaaaaaaaa                               40

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
gctgcgttga tcatcgatgc                                                     20

<210> SEQ ID NO 57
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
gctgcgttga tcatcgatgc gctgcgttga tcatcgatgc                               40

<210> SEQ ID NO 58
<211> LENGTH: 50
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 58
gctgcgttga tcatcgatgc aaaaaaaaaa gctgcgttga tcatcgatgc              50

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
gctgcgttga tcatcgatgc aaaaaaaaaa                                    30

<210> SEQ ID NO 60
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 60
gctgcgttga tcatcgatgc aaaaaaaaaa aaaaaaaaaa                         40

<210> SEQ ID NO 61
<211> LENGTH: 23
<212> TYPE: DNA
<213> ORGANISM: Pythium torulosum

<400> SEQUENCE: 61
ggagagaaat ggcagaatgt gag                                           23

<210> SEQ ID NO 62
<211> LENGTH: 22
<212> TYPE: DNA
<213> ORGANISM: Pythium volutum

<400> SEQUENCE: 62
ggagagaaat ggcagatgtg ag                                            22

<210> SEQ ID NO 63
<211> LENGTH: 24
<212> TYPE: DNA
<213> ORGANISM: Pythium torulosum

<400> SEQUENCE: 63
aggagagaaa tggcagaatg tgag                                          24

<210> SEQ ID NO 64
<211> LENGTH: 23
<212> TYPE: DNA
<213> ORGANISM: Pythium volutum

<400> SEQUENCE: 64
aggagagaaa tggcagatgt gag                                           23

<210> SEQ ID NO 65
<211> LENGTH: 24
<212> TYPE: DNA
```

```
<213> ORGANISM: Pythium sp.

<400> SEQUENCE: 65
gaggtgtacc tgtcttgtgt gagg                                          24

<210> SEQ ID NO 66
<211> LENGTH: 23
<212> TYPE: DNA
<213> ORGANISM: Fusarium equiseti

<400> SEQUENCE: 66
tagcgtagta gctaacacct cgt                                           23

<210> SEQ ID NO 67
<211> LENGTH: 24
<212> TYPE: DNA
<213> ORGANISM: Fusarium solani

<400> SEQUENCE: 67
cctgtgaaca tacctaaaac gttg                                          24

<210> SEQ ID NO 68
<211> LENGTH: 21
<212> TYPE: DNA
<213> ORGANISM: Fusarium equiseti

<400> SEQUENCE: 68
cctgtgaaca tacctacgtt g                                             21

<210> SEQ ID NO 69
<211> LENGTH: 24
<212> TYPE: DNA
<213> ORGANISM: Fusarium solani

<400> SEQUENCE: 69
ttattcaact catcaaccct gtga                                          24

<210> SEQ ID NO 70
<211> LENGTH: 26
<212> TYPE: DNA
<213> ORGANISM: Fusarium sp.

<400> SEQUENCE: 70
ttatacaact catcaaaccc ctgtga                                        26

<210> SEQ ID NO 71
<211> LENGTH: 24
<212> TYPE: DNA
<213> ORGANISM: Fusarium equiseti

<400> SEQUENCE: 71
cgtccctcaa atcgattggg ggtc                                          24

<210> SEQ ID NO 72
<211> LENGTH: 21
<212> TYPE: DNA
<213> ORGANISM: Fusarium equiseti

<400> SEQUENCE: 72
gttgggactc gcggtaaccc g                                             21

<210> SEQ ID NO 73
<211> LENGTH: 44
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
tgtaactctc cgcgtagtaa tatgtaactc tccgcgtagt aata                44

<210> SEQ ID NO 74
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
gttgaccctc cacccgtgtc gattagttga ccctccaccc gtgtcgatta          50

<210> SEQ ID NO 75
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75
agcgtccgta acaacctctc aagcctagcg tccgtaacaa cctctcaagc ct       52

<210> SEQ ID NO 76
<211> LENGTH: 54
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 76
gagcgtccgt aacaacctct caagcctgag cgtccgtaac aacctctcaa gcct     54

<210> SEQ ID NO 77
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 77
tttcggagcg cagcacatat tttgtttcgg agcgcagcac atattttg            48

<210> SEQ ID NO 78
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 78
ctgggagact cgccttaaaa cgattgctgg gagactcgcc ttaaaacgat tg       52

<210> SEQ ID NO 79
<211> LENGTH: 54
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 79
gcttggtgtt gggcgttttt tgtctccgct tggtgttggg cgttttttgt ctcc          54

<210> SEQ ID NO 80
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
catttttaac ttttgacctc ggatcatttt taacttttga cctcggat                 48

<210> SEQ ID NO 81
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 81
ctaccagggg acgtggcgcc cgccgctacc aggggacgtg gcgcccgccg               50

<210> SEQ ID NO 82
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82 ccagggacg tggcgcccgc cggaccaggg gacgtggcgc ccgccgga                  48

<210> SEQ ID NO 83
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
acgacgtttc ttctgagtgg cacaacgacg tttcttctga gtggcaca                 48

<210> SEQ ID NO 84
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
ctgagtggca caagcaaata attctgagtg gcacaagcaa ataatt                   46

<210> SEQ ID NO 85
<211> LENGTH: 42
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 85
cagaaaccgc tctatactcg gcagaaaccg ctctatactc gg                          42

<210> SEQ ID NO 86
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 86
gcctgattct ccccatgtct tgcctgattc tccccatgtc tt                          42

<210> SEQ ID NO 87
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
acgatagcct gaagcgcagc acatacgata gcctgaagcg cagcacat                    48

<210> SEQ ID NO 88
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 88
cagcgtcagt aacaagtaat tcagcgtcag taacaagtaa tt                          42

<210> SEQ ID NO 89
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89
agaatagagt gcacttgatt gtggctagaa tagagtgcac ttgattgtgg ct               52

<210> SEQ ID NO 90
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
ttattaggag agttacatta cccttattag gagagttaca ttaccc                      46

<210> SEQ ID NO 91
<211> LENGTH: 52
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 91
cttggttgca tgatttgaaa gagtcacttg gttgcatgat ttgaaagagt ca         52

<210> SEQ ID NO 92
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 92
ttaaaaagac ttggttgcat ttaaaaagac ttggttgcat                       40

<210> SEQ ID NO 93
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 93
gcattcttta ttgaatgttc acagcattct ttattgaatg ttcaca               46

<210> SEQ ID NO 94
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 94
cacttctttg catgatttga aagacacttc tttgcatgat ttgaaaga             48

<210> SEQ ID NO 95
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
aatcttaccc aaacttttaa cacaatctta cccaaacttt taacac               46

<210> SEQ ID NO 96
<211> LENGTH: 54
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 96
gtttagtgga tgttgagtgt tgctgtcgtt tagtggatgt tgagtgttgc tgtc      54

<210> SEQ ID NO 97
<211> LENGTH: 50
<212> TYPE: DNA
<213> ORGANISM: Artificial Sequence
<220> FEATURE:
<223> OTHER INFORMATION: Description of Artificial Sequence: Synthetic probe

<400> SEQUENCE: 97
acgtaacttc tttattgaat gttgcacgta acttctttat tgaatgttgc         50

<210> SEQ ID NO 98
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98 gtcactttc tataagttgg atgtcacttt tctataagtt ggat                44

<210> SEQ ID NO 99
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99
catcttattt aagggagact ccatcttatt taagggagac tc                 42

<210> SEQ ID NO 100
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100
gagactccta aaacccaat gagactccta aaacccaat                      40

<210> SEQ ID NO 101
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
acttttaaaa acttggttgc atgaactttt aaaaacttgg ttgcatga           48

<210> SEQ ID NO 102
<211> LENGTH: 54
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
ttagtggatg ttgagtgttg ctgtaccttg gtggatgttg agtgttgctg tacc    54

<210> SEQ ID NO 103
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 103
cacttgccat cttgtttgtt acacttgcca tcttgtttgt ta                42

<210> SEQ ID NO 104
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104
gagtatacgt aacattctta attgagagta tacgtaacat tcttaattga         50

<210> SEQ ID NO 105
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
gccatctttt ttgtaacaag agacgccatc tttttgtaa caagagac            48

<210> SEQ ID NO 106
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 106
cccaatatct atttttttta agacctccca atatctattt tttttaagac ct      52

<210> SEQ ID NO 107
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107
aacaagagac tcctaaaacc caaacaagag actcctaaaa ccca               44

<210> SEQ ID NO 108
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
tgggttttag gagtctcttg tttgggtttt aggagtctct tgtt               44

<210> SEQ ID NO 109
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
gttctgtgcc ttctcttggg aggttctgtg ccttctcttg ggag                    44

<210> SEQ ID NO 110
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 110
gaaggttggc tgcaaatgta gtgaaggttg gctgcaaatg tagt                    44

<210> SEQ ID NO 111
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111
ctgtatgcgc ggtcttccga tgtactgtat gcgcggtctt ccgatgta                48

<210> SEQ ID NO 112
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 112
cttgtgtttg agagaagtgc tgacccttgt gtttgagaga agtgctgacc              50

<210> SEQ ID NO 113
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 113
gcggttttgc cgatgtactt ttaaacgcgg ttttgccgat gtacttttaa ac           52

<210> SEQ ID NO 114
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 114
gtacctgtct tgtgtgaggc aacggtacct gtcttgtgtg aggcaacg                48

<210> SEQ ID NO 115
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 115
tgtcttgtgt gaggcaacgg tctgtgtctt gtgtgaggca acggtctg                    48

<210> SEQ ID NO 116
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 116
gtacctgtct tgtgtgaggc aacgggtacc tgtcttgtgt gaggcaacgg                  50

<210> SEQ ID NO 117
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 117
tgtaattttg ttttgtgcct tctttctgta attttgtttt gtgccttctt tc               52

<210> SEQ ID NO 118
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 118
gaaagaaggc acaaaacaaa attacagaaa gaaggcacaa aacaaaatta ca               52

<210> SEQ ID NO 119
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 119
tacctgattt gtgtgaggca atggttacct gatttgtgtg aggcaatggt                  50

<210> SEQ ID NO 120
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 120
tcatgttctg tgctctctct cgggatcatg ttctgtgctc tctctcggga                  50

<210> SEQ ID NO 121
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 121

```
cgttgactcc cttttcggag gagaacgttg actcccttttt cggaggagaa         50
```

<210> SEQ ID NO 122
<211> LENGTH: 54
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 122

```
gcttaattgt ggtctgccga tgtatttgct taattgtggt ctgccgatgt attt    54
```

<210> SEQ ID NO 123
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 123

```
gagtcggcta aacgaaggtc ggggagtcgg ctaaacgaag gtcggg              46
```

<210> SEQ ID NO 124
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 124

```
gactccggtt tttctattgc gttgctgact ccggtttttc tattgcgttg ct      52
```

<210> SEQ ID NO 125
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 125

```
ttggagaagg agcagaggtg aagttggaga aggagcagag gtgaag              46
```

<210> SEQ ID NO 126
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 126

```
ctccagagca cgctaccgag gtctccagag cacgctaccg aggt                44
```

<210> SEQ ID NO 127
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 127

```
ggactgatgt gcgcttgtcg catgtggact gatgtgcgct tgtcgcatgt          50
```

```
<210> SEQ ID NO 128
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 128
ttaaaccata ccataagtac tgattttaaa ccataccata agtactgatt              50

<210> SEQ ID NO 129
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 129
tctccgctga gagtttgtgt gtgtctccgc tgagagtttg tgtgtg                  46

<210> SEQ ID NO 130
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 130
ctctccgctg agagtttgtg tgtgctctcc gctgagagtt tgtgtgtg                48

<210> SEQ ID NO 131
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 131
gctgctcttg gacgccctgt tttcgctgct cttggacgcc ctgttttc                48

<210> SEQ ID NO 132
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 132
gctgctcttg gacgccctgt tgctgctctt ggacgccctg tt                      42

<210> SEQ ID NO 133
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 133
gactgtttgc aatttattgt gagactgttt gcaatttatt gtga                    44
```

```
<210> SEQ ID NO 134
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 134
gaaagtttat ggttttaatc tagaaagttt atggttttaa tcta                    44

<210> SEQ ID NO 135
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 135
gattagagat ggcagaatgt gaggtggatt agagatggca gaatgtgagg tg           52

<210> SEQ ID NO 136
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 136
gctctgcgcg agtgggcgac ttcggtgctc tgcgcgagtg ggcgacttcg gt           52

<210> SEQ ID NO 137
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 137
cctgtcttgt gtggggcaat ggtctgcctg tcttgtgtgg ggcaatggtc tg           52

<210> SEQ ID NO 138
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 138
cctgtcttgt gtggggcaat ggtcctgtct tgtgtgggc aatggt                   46

<210> SEQ ID NO 139
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 139
ggttgtccgc aagtgtagtt aattcggttg tccgcaagtg tagttaattc              50
```

```
<210> SEQ ID NO 140
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 140
agatggcaga tgtgaggtgt ctagatggca gatgtgaggt gtct                    44

<210> SEQ ID NO 141
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 141
gtgtctgaga gaagtgtgac ctgtgtctga gagaagtgtg acct                    44

<210> SEQ ID NO 142
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 142
agtggttatt gctcttggac gcagtggtta ttgctcttgg acgc                    44

<210> SEQ ID NO 143
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 143
aacgaatgta attgatgtaa cgaacgaatg taattgatgt aacg                    44

<210> SEQ ID NO 144
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 144
ctggatctca gtgttatgct tggctggatc tcagtgttat gcttgg                  46

<210> SEQ ID NO 145
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 145
accgcttcta atagtccatt gacaccgctt ctaatagtcc attgac                  46

<210> SEQ ID NO 146
```

<210> SEQ ID NO 146
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 146
gtaacgcatc taatactaag tttgtaacgc atctaatact aagttt            46

<210> SEQ ID NO 147
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 147
ccgtccaata cataaaatct taccgtccaa tacataaaat ctta              44

<210> SEQ ID NO 148
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 148
taatcagaat gtaatcgatg taaacgtaat cagaatgtaa tcgatgtaaa cg     52

<210> SEQ ID NO 149
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 149
gtaaacgcat ctataaacta aggtaaacgc atctataaac taag              44

<210> SEQ ID NO 150
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 150
ggcttttgtt ttggatttgg aggtggcttt tgttttggat tggaggt           48

<210> SEQ ID NO 151
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 151
gtccctgtag actctgcttc agtccctgta gactctgctt ca                42

<210> SEQ ID NO 152
<211> LENGTH: 42

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 152
ctagtgtttc tagtatgtgc actagtgttt ctagtatgtg ca                         42

<210> SEQ ID NO 153
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 153
gtaatagatc tatgtggata cggtaataga tctatgtgga tacg                       44

<210> SEQ ID NO 154
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 154
tgaagcagag tctacaggga ctgaagcaga gtctacaggg ac                         42

<210> SEQ ID NO 155
<211> LENGTH: 54
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 155
cttctgtaat agatctatgt ggatacgctt ctgtaataga tctatgtgga tacg            54

<210> SEQ ID NO 156
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 156
catgaatctc tcaaatacaa tgatttcatg aatctctcaa atacaatgat tt              52

<210> SEQ ID NO 157
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 157
catgaatctc tcaaatacaa tgacatgaat ctctcaaata caatga                     46

<210> SEQ ID NO 158
<211> LENGTH: 44
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 158
ccttctgtaa tagatctatg tgccttctgt aatagatcta tgtg                    44

<210> SEQ ID NO 159
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 159
ttatacacac acaatagtca ttgttataca cacacaatag tcattg                  46

<210> SEQ ID NO 160
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 160
cctgtgcacc ttttgtagta ttaccctgtg cacctttgt agtattac                 48

<210> SEQ ID NO 161
<211> LENGTH: 54
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 161
caaatgtatt agctggggtt tatatagcaa atgtattagc tggggtttat atag         54

<210> SEQ ID NO 162
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 162
tggaagctgt tggcgcaagt cgatggaagc tgttggcgca agtcga                  46

<210> SEQ ID NO 163
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 163
tattttgaat cattattatt tggactattt tgaatcatta tatttggac               50

<210> SEQ ID NO 164
<211> LENGTH: 46
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 164
cttggaagtt tgtcggcgca agtcttggaa gtttgtcggc gcaagt                    46

<210> SEQ ID NO 165
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 165
tgagtgtcat gaatctctca aatatgagtg tcatgaatct ctcaaata                  48

<210> SEQ ID NO 166
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 166
atttggactt ggaagtttgt cggcatttgg acttggaagt tgtcggc                   48

<210> SEQ ID NO 167
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 167
ttggaagttt gtcggcgcaa gtttggaagt tgtcggcgc aagt                       44

<210> SEQ ID NO 168
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 168 tccaacccctt gtgtatctct accatccaac ccttgtgtat ctctacca                 48

<210> SEQ ID NO 169
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 169
ccttgtgtat ctctaccatg ttccttgtgt atctctacca tgtt                      44

<210> SEQ ID NO 170
<211> LENGTH: 48
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 170
acagcctcag cgccctccgg ggccacagcc tcagcgccct ccggggcc                    48

<210> SEQ ID NO 171
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 171
aggaaaatca caactctgaa ttgaggaaaa tcacaactct gaattg                      46

<210> SEQ ID NO 172
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 172
atggggttct gcttctaatc gtcatggggt tctgcttcta atcgtc                      46

<210> SEQ ID NO 173
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 173
ctctttgtgg tgccagacta tgctctttgt ggtgccagac tatg                        44

<210> SEQ ID NO 174
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 174
gtgataatta tctacgctgt ggttgtgata attatctacg ctgtggtt                    48

<210> SEQ ID NO 175
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 175
gctgcgaatt taactatggg gctgcgaatt taactatggg                             40

<210> SEQ ID NO 176
<211> LENGTH: 42
<212> TYPE: DNA
<213> ORGANISM: Artificial Sequence
<220> FEATURE:
<223> OTHER INFORMATION: Description of Artificial Sequence: Synthetic probe

<400> SEQUENCE: 176
ctacgctgtt ggtcttgtga actacgctgt tggtcttgtg aa                          42

<210> SEQ ID NO 177
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 177
ggtcttgtga agcactttat tgtggtcttg tgaagcactt tattgt                      46

<210> SEQ ID NO 178
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 178
gttacgaggt tctgcttcta atcgttacga ggttctgctt ctaatc                      46

<210> SEQ ID NO 179
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 179
ttctaatcgt cctttactgc ttctaatcgt cctttactgc                             40

<210> SEQ ID NO 180
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 180
ctgttgcttc ggcggacgat ggctgttgct tcggcggacg atgg                        44

<210> SEQ ID NO 181
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 181
gacgccgccg gaggttacaa accgacgccg ccggaggtta caaacc                      46

<210> SEQ ID NO 182
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 182
ggacgccgcc ggaggttaca ggacgccgcc ggaggttaca                            40

<210> SEQ ID NO 183
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 183
ccgcccggcg gtcggggccc ccaccgcccg gcggtcgggg ccccca                     46

<210> SEQ ID NO 184
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 184
caaccctcaa gccccggctt ggtcaaccct caagccccgg cttggt                     46

<210> SEQ ID NO 185
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 185
gcatctctga gcctaaaaga caagcatctc tgagcctaaa agacaa                     46

<210> SEQ ID NO 186
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 186
gaaccctcgc tcggcccgtc accgaaccct cgctcggccc gtcacc                     46

<210> SEQ ID NO 187
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 187
gcctcggctt ggtgttgggg cgcctcggct tggtgttggg gc                         42

<210> SEQ ID NO 188
<211> LENGTH: 48
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 188
cacgcccgcc ggaggttcaa aactcacgcc cgccggaggt tcaaaact                    48

<210> SEQ ID NO 189
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 189
cgccggaggt tcaaaactct tattcgccgg aggttcaaaa ctcttatt                    48

<210> SEQ ID NO 190
<211> LENGTH: 54
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 190
gtgctccagc cgctaaaccc ccaattcgtg ctccagccgc taaaccccca attc             54

<210> SEQ ID NO 191
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 191
cgccgccgga ggttcaaaac ccgccgccgg aggttcaaaa cc                          42

<210> SEQ ID NO 192
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 192
ccgccggagg ttcaaaaccc tccgccggag gttcaaaacc ct                          42

<210> SEQ ID NO 193
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 193
aacgcgccct cgctcggcgg caacgcgccc tcgctcggcg gc                          42

<210> SEQ ID NO 194
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 194
```
gctccgagcg cagtagcacg cgctccgagc gcagtagcac gc                42

<210> SEQ ID NO 195
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 195
ggttggcgcc ggtgcccaga tgggttggcg ccggtgccca gatg              44

<210> SEQ ID NO 196
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 196
gtcgccgccg gaggttcgaa accgtcgccg ccggaggttc gaaacc            46

<210> SEQ ID NO 197
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 197
ccgccggagg ttcgaaaccc tccgccggag gttcgaaacc ct                42

<210> SEQ ID NO 198
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 198
ttcgaaaccc tgaattctag tgttcgaaac cctgaattct agtg              44

<210> SEQ ID NO 199

<400> SEQUENCE: 199

000

<210> SEQ ID NO 200
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 200
gaggtcgccg ccggaggttc gaagaggtcg ccgccggagg ttcgaa            46

<210> SEQ ID NO 201
<211> LENGTH: 50
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 201
gcctggaggt cgccgccgga ggttcgcctg gaggtcgccg ccggaggttc            50

<210> SEQ ID NO 202
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 202
ccagatgggc ctggaggtcg ccgcccagat gggcctggag gtcgccgc              48

<210> SEQ ID NO 203
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 203
aagtacatcg gcggacccgc tgggaagtac atcggcggac ccgctggg              48

<210> SEQ ID NO 204
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 204
ggcggacccg ctggggccct gagggcggac ccgctggggc cctgag                46

<210> SEQ ID NO 205
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 205
cgcctcgctc ggtggatccc cggaggcgcc tcgctcggtg atccccgga gg          52

<210> SEQ ID NO 206
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 206
ccggagggca ttccagccgc taaaccggag ggcattccag ccgctaaa              48

<210> SEQ ID NO 207
<211> LENGTH: 52
<212> TYPE: DNA
<213> ORGANISM: Artificial Sequence
```

<220> FEATURE:
<223> OTHER INFORMATION: Description of Artificial Sequence: Synthetic
      probe

<400> SEQUENCE: 207
ctggaaacag tgctgccacc ggtggactgg aaacagtgct gccaccggtg ga          52

<210> SEQ ID NO 208
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 208
aagccggcca gacgacagcc ataaaagccg gccagacgac agccataa              48

<210> SEQ ID NO 209
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 209
gccagacgac agccataaac cgccagacga cagccataaa cc                    42

<210> SEQ ID NO 210
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 210
ctggaaacag tgctgccacc ggtctggaaa cagtgctgcc accggt                46

<210> SEQ ID NO 211
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 211
ggtggatggt gctgtctctc gggtggatgg tgctgtctct cg                    42

<210> SEQ ID NO 212
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 212
tggactacct aaactctgtt atggactacc taaactctgt ta                    42

<210> SEQ ID NO 213
<211> LENGTH: 42
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 213
gtcaatctga atcaaactaa ggtcaatctg aatcaaacta ag                          42

<210> SEQ ID NO 214
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 214
cggagtcggt tcgtgctctg acggagtcgg ttcgtgctct ga                          42

<210> SEQ ID NO 215
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 215
ctcggtggtt agtactctct ctcgctcggt ggttagtact ctctctcg                    48

<210> SEQ ID NO 216
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 216
cggtggttag tgctctctct cggcggtggt tagtgctctc tctcgg                      46

<210> SEQ ID NO 217
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 217
tctctctcgg gagggtgctg cctctctctc gggagggtgc tgcc                        44

<210> SEQ ID NO 218
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 218
gtaattactt atctcgcttc ttgtaattac ttatctcgct tctt                        44

<210> SEQ ID NO 219
<211> LENGTH: 46
<212> TYPE: DNA
<213> ORGANISM: Artificial Sequence
<220> FEATURE:
<223> OTHER INFORMATION: Description of Artificial Sequence: Synthetic probe

<400> SEQUENCE: 219
cctttgggtg tccgagttgt attcctttgg gtgtccgagt tgtatt        46

<210> SEQ ID NO 220
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 220
tttccgcgct ggactgtgta aatttccgcg ctggactgtg taaa        44

<210> SEQ ID NO 221
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 221
cgcgttgtat gagactcagc ctcgcgttgt atgagactca gcct        44

<210> SEQ ID NO 222
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 222
ggcatccttt gggtgtccga gttgggcatc ctttgggtgt ccgagttg        48

<210> SEQ ID NO 223
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 223
taaagcaatt ggcagcctat atcttaaagc aattggcagc ctatatct        48

<210> SEQ ID NO 224
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 224
agcacaaact gcatgggcgg agcacaaact gcatgggcgg        40

<210> SEQ ID NO 225
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 225
cccattgaac ctatttattt tcccattgaa cctatttatt tt                             42

<210> SEQ ID NO 226
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 226
agcaattggc agcctatatc tggagcaatt ggcagcctat atctgg                         46

<210> SEQ ID NO 227
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 227
tcttactgcc agttatatag gcactcttac tgccagttat ataggcac                       48

<210> SEQ ID NO 228
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 228
gtgtagaaca aactacgcag acgtgtagaa caaactacgc agac                           44

<210> SEQ ID NO 229
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 229
ccaataagcc tttttatcac ccaataagcc tttttatcac                                40

<210> SEQ ID NO 230
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 230
tctactccac tgcgtttgga ctcgtctact ccactgcgtt tggactcg                       48

<210> SEQ ID NO 231
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 231
agaacatagg ccccaagctg tagcagaaca taggccccaa gctgtagc                48

<210> SEQ ID NO 232
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 232
aaggcctctt ctattaccct tgtaaggcct cttctattac ccttgt                  46

<210> SEQ ID NO 233
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 233
atcattacat tagaacatag gccatcatta cattagaaca taggcc                  46

<210> SEQ ID NO 234
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 234
ggtgttttgt cctctccatt gcgggtgttt tgtcctctcc attgcg                  46

<210> SEQ ID NO 235
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 235
atatcaataa cacaaactaa caagatatca ataacacaaa ctaacaag                48

<210> SEQ ID NO 236
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 236
ctggcatcct ccgggtgtcc gagtctggca tcctccgggt gtccgagt                48

<210> SEQ ID NO 237
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 237
cttgttagtt tgtgttattg atatcttgtt agtttgtgtt attgatat    48

<210> SEQ ID NO 238
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 238
actcggacac ccggaggatg ccagactcgg acacccggag gatgccag    48

<210> SEQ ID NO 239
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 239
ataaagggag gtcatgacgg tataaaggga ggtcatgacg gt    42

<210> SEQ ID NO 240
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 240
ctaataaagg gaggtcatga cgctaataaa gggaggtcat gacg    44

<210> SEQ ID NO 241
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 241
cgtcatgacc tccctttatt agcgtcatga cctcccttta ttag    44

<210> SEQ ID NO 242
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 242
accgtcatga cctccctttta taccgtcatg acctcccttt at    42

<210> SEQ ID NO 243
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 243
agtgaaatgc gtaagatcgg gaggaagtga aatgcgtaag atcgggagga             50

<210> SEQ ID NO 244
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 244
cacggaactt tccagagatg gattgcacgg aactttccag agatggattg             50

<210> SEQ ID NO 245
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 245
cacagtggta gcaataccat gggtgcacag tggtagcaat accatgggtg             50

<210> SEQ ID NO 246
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 246
cacagtggta gcaataccat gcacagtggt agcaatacca tg                     42

<210> SEQ ID NO 247
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 247
gggcgtcttg tcttttggct ctgggcgtct tgtcttttgg ctct                   44

<210> SEQ ID NO 248
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 248
ggctctttgc ccaaagactc ggctctttgc ccaaagactc                        40

<210> SEQ ID NO 249
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 249
cgccaggacc acaccataaa cctcgccagg accacaccat aaacct                 46

<210> SEQ ID NO 250
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 250
gccgccagga ccacaccata agccgccagg accacaccat aa                          42

<210> SEQ ID NO 251
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 251
cgttaccaaa ctgttgcctc ggccgttacc aaactgttgc ctcggc                      46

<210> SEQ ID NO 252
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 252
caaccctcga acccctccgg gcaaccctcg aacccctccg gg                          42

<210> SEQ ID NO 253
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 253
gtattctggc gggcatgcct gtccgtattc tggcgggcat gcctgtcc                    48

<210> SEQ ID NO 254
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 254
gatctgtatc cgcccccgac ccgatctgta tccgcccccg accc                        44

<210> SEQ ID NO 255
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 255
gtatccgccc ccgacccttc gatcgtatcc gcccccgacc cttcgatc                    48

<210> SEQ ID NO 256
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 256
gagggtagcg ccgtttcatg gtcggagggt agcgccgttt catggtcg                    48

<210> SEQ ID NO 257
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 257
ctaatctagg agtggcatcg aactaatcta ggagtggcat cgaa                        44

<210> SEQ ID NO 258
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 258
cgcccatatc gagttttgcc tcggcgccca tatcgagttt tgcctcgg                    48

<210> SEQ ID NO 259
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 259
ttacaatgaa atcgactggt aatgcttaca atgaaatcga ctggtaatgc                  50

<210> SEQ ID NO 260
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 260
acaatgaaat cgactggtaa tgcacaatga aatcgactgg taatgc                      46

<210> SEQ ID NO 261
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 261
gcacacttgt cttgacttta ttcgcacact tgtcttgact ttattc                      46

```
<210> SEQ ID NO 262
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 262
ggagcatgtg cacacttgtc ttggagcatg tgcacacttg tctt                    44

<210> SEQ ID NO 263
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 263
cgagttgtga tggggcttgg atccgagttg tgatggggct tggatc                  46

<210> SEQ ID NO 264
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 264
tccggatgtg aggaattgct gagttccgga tgtgaggaat tgctgagt                48

<210> SEQ ID NO 265
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 265
tacctctcct tcaagtacta tgttacctct ccttcaagta ctatgt                  46

<210> SEQ ID NO 266
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 266
attaaattct caacccctct agctttatta aattctcaac ccctctagct tt           52

<210> SEQ ID NO 267
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 267
aaattctcaa cccctctagc ttaaattctc aacccctcta gctt                    44

<210> SEQ ID NO 268
```

```
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 268
tggacttcat tttcatccac ctgtggactt cattttcatc cacctg            46

<210> SEQ ID NO 269
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 269 tcttttcct gttagagtct atgttctttt tcctgttaga gtctatgt            48

<210> SEQ ID NO 270
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 270
ttgtagtctt tttcaggtat tgttgtagtc tttttcaggt attg               44

<210> SEQ ID NO 271
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 271
gttgtaaagg agagcttgga ttgtgttgta aaggagagct tggattgt           48

<210> SEQ ID NO 272
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 272
ttggtattcc gagaggcatg cctgttggta ttccgagagg catgcctg           48

<210> SEQ ID NO 273
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 273
ttgcgcctct tggtattccg agaggttgcg cctcttggta ttccgagagg         50

<210> SEQ ID NO 274
<211> LENGTH: 44
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 274
catgtagtat gttgccagaa tgcatgtagt atgttgccag aatg                        44

<210> SEQ ID NO 275
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 275
accatgtagt atgttgccag aatgaccatg tagtatgttg ccagaatg                    48

<210> SEQ ID NO 276
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 276
tatcacaaac catgtagtat gtttatcaca aaccatgtag tatgtt                      46

<210> SEQ ID NO 277
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 277
acatagaacg atctcatatt gaaacataga acgatctcat attgaa                      46

<210> SEQ ID NO 278
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 278
actcttattg tatgttacat agaacactct tattgtatgt tacatagaac                  50

<210> SEQ ID NO 279
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 279
agagtcatta aattctcaac cttagagtca ttaaattctc aacctt                      46

<210> SEQ ID NO 280
<211> LENGTH: 48
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 280
caaggcttgg atgtgagagt tgctcaaggc ttggatgtga gagttgct                  48

<210> SEQ ID NO 281
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 281
aagggacggc ccgccgcagg aacccaaggg acggcccgcc gcaggaaccc                50

<210> SEQ ID NO 282
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 282
ctgcactccc caaatacatt ggcgctgcac tccccaaata cattggcg                  48

<210> SEQ ID NO 283
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 283
gctgcactcc ccaaatacat tggcgctgca ctccccaaat acattggc                  48

<210> SEQ ID NO 284
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 284
ggactcgcgt taattcgcgt tccggactcg cgttaattcg cgttcc                    46

<210> SEQ ID NO 285
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 285
cgcgttcctc aaattgattg gcggtcgcgt tcctcaaatt gattggcggt                50

<210> SEQ ID NO 286
<211> LENGTH: 48
<212> TYPE: DNA
<213> ORGANISM: Artificial Sequence
```

<220> FEATURE:
<223> OTHER INFORMATION: Description of Artificial Sequence: Synthetic
      probe

<400> SEQUENCE: 286
tgttgcctcg gcggatcagc ccgctgttgc ctcggcggat cagcccgc          48

<210> SEQ ID NO 287
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 287
aaataaatca aactttcaa caaaaataaa tcaaaacttt caacaa              46

<210> SEQ ID NO 288
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 288
cctcagcctg gagttccccc ggacctcagc ctggagttcc cccgga            46

<210> SEQ ID NO 289
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 289
acattgagcc tgttgctggg gaagatacat tgagcctgtt gctggggaag at     52

<210> SEQ ID NO 290
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 290
ctcagcctgg agttccccg gactcagcct ggagttcccc cgga               44

<210> SEQ ID NO 291
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 291
catatcgagc tgttgctgg ggaagacata tcgagcctgt tgctgggaa ga       52

<210> SEQ ID NO 292
<211> LENGTH: 52
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 292
tatcgagcct gttgctgggg aagacatatc gagcctgttg ctggggaaga ca                 52

<210> SEQ ID NO 293
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 293
agtcctcaac ctggggttcc gccgagtcct caacctgggg ttccgccg                      48

<210> SEQ ID NO 294
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 294
agtcctcaac ctggggttcc gccggaagtc ctcaacctgg ggttccgccg ga                 52

<210> SEQ ID NO 295
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 295
cgagtaagat ggaacatttt ggcgagtaag atggaacatt ttgg                          44

<210> SEQ ID NO 296
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 296
tgccaaaatt cgataccata gttctgccaa aattcgatac catagttc                      48

<210> SEQ ID NO 297
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 297
gaatgccaaa attcgatacc atagtgaatg ccaaaattcg ataccatagt                    50

<210> SEQ ID NO 298
<211> LENGTH: 50
<212> TYPE: DNA
<213> ORGANISM: Artificial Sequence
<220> FEATURE:
<223> OTHER INFORMATION: Description of Artificial Sequence: Synthetic

```
              probe

<400> SEQUENCE: 298
ctatccattt tgaaatcttg gtgcactatc cattttgaaa tcttggtgca              50

<210> SEQ ID NO 299
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 299
gcaactcctt caataccgta tcaagcaact ccttcaatac cgtatcaa                48

<210> SEQ ID NO 300
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 300
attatcttct ggaactttc tggaattatc ttctggaact tttctgga                48

<210> SEQ ID NO 301
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 301
tgcaactcct tcaataccgt atcaatgcaa ctccttcaat accgtatcaa              50

<210> SEQ ID NO 302
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 302
tcctccgttt attgatttgc tcctccgttt attgatttgc                        40

<210> SEQ ID NO 303
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 303
tcctccgttt attgaaatgc tcctccgttt attgaaatgc                        40

<210> SEQ ID NO 304
<211> LENGTH: 40
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 304
tcctccgttt attggtatgc tcctccgttt attggtatgc                    40

<210> SEQ ID NO 305
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 305
cgatctattc attcaatatt tccgatctat tcattcaata tttc               44

<210> SEQ ID NO 306
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 306
tctagcacac gaaagtcgaa gttctagcac acgaaagtcg aagt               44

<210> SEQ ID NO 307
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 307
atgtcaccac aaacagagac taaagcatgt caccacaaac agagactaaa gc      52

<210> SEQ ID NO 308
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 308
atgtcaccac aaacagaaac atgtcaccac aaacagaaac                    40
```

DIMERIC DIAGNOSTIC ARRAYS

RELATED APPLICATION(S)

This application claims the benefit of priority of U.S. Provisional Application Ser. No. 61/476,143 filed on Apr. 15, 2011, which application is herein incorporated by reference.

Sequence Listing

The instant application contains a Sequence Listing which has been submitted in ASCII format via EFS-Web and is hereby incorporated by reference in its entirety. Said ASCII copy, created on Sep. 4, 2012, is named 08035006.txt and is 68,827 bytes in size.

BACKGROUND

Detection and identification of pathogens, e.g., microbial plant pathogens, poses a challenge because different pathogens may infect the same host concurrently and may produce similar symptoms. In the absence of clear distinctive symptoms and signs, plant disease diagnosticians may use the host identity, time of the year and prevailing weather conditions to associate the pathogen with the disease. Accurate pathogen identification is the first step in disease management. Misidentification of a pathogen may lead to poor disease control, crop damage and ultimately reduced yield. There is therefore a need for improved disease surveillance, more rapid diagnoses, and accurate remedial measures in the shortest time possible.

SUMMARY OF CERTAIN EMBODIMENTS OF THE INVENTION

Certain embodiments of the present invention provide an array that comprises a first plurality of dimeric probes that hybridize to a first target nucleic acid sequence, wherein the dimeric probes each comprise a first hybridizing nucleic acid sequence and a second hybridizing nucleic acid sequence linked together, wherein the first and second hybridizing nucleic acid sequences are the same and hybridize to the first target nucleic acid sequence. In certain embodiments, the dimeric probe comprises a third hybridizing nucleic acid sequence that hybridizes to the first target nucleic acid sequence and is the same as the first hybridizing a second hybridizing nucleic acid sequences.

Redundancy in the array may improve accuracy and analytical power through over-representation. As used herein, the phrase a "plurality of dimeric probes" means at least two (e.g., 2, 3, 4, 5, 6, 7, 8, 9, 10) probes that hybridize to the same target nucleic acid sequence.

In certain embodiments, the first plurality of dimeric probes comprises at least two (e.g., 2, 3, 4, 5, 6, 7, 8, 9, 10) probes.

In certain embodiments, the first and second hybridizing nucleic acid sequences are linked directly together.

In certain embodiments, the first and second hybridizing nucleic acid sequences are linked together via a nucleic acid linker sequence.

In certain embodiments, the nucleic acid linker sequence is a poly-adenine linker (e.g., about 5-15, e.g., about 10 nucleotides in length).

In certain embodiments, the dimeric probes are about 40-60 nucleotide in length.

In certain embodiments, the dimeric probes are about 40-48 nucleotide in length.

In certain embodiments, the dimeric probes are about 50-58 nucleotide in length.

In certain embodiments, the array comprises a second plurality of dimeric probes that hybridize to a second target nucleic acid sequence.

In certain embodiments, the second plurality of dimeric probes comprises at least two (e.g., 2, 3, 4, 5, 6, 7, 8, 9, 10) probes.

As redundancy may improve the accuracy and analytical power of the array, probes that recognize different target nucleic acid sequences in the same pathogen may be used.

Accordingly, in certain embodiments, the first and second pluralities of probes hybridize to target nucleic acid sequences in the same pathogen.

The array may also be designed to detect more than one type of pathogen. DNA sequences available in publicly accessible databases (e.g., GenBank) allow for the creation of signature probes specific to a species or infra-species target. Accordingly, one skilled in the art may design a dimeric probe as described herein, which is specific to any given species or sub-species, wherein the genomic sequence of the species or sub-species is known (e.g., full or partial), using techniques known in the art or described herein (e.g., Example 1 or 2).

Accordingly, in certain embodiments, the first and second pluralities of probes hybridize to target nucleic acid sequences in different pathogens.

In certain embodiments, the array comprises more than two pluralities of dimeric probes (e.g., 3-6) that hybridize to different target nucleic acid sequences.

In certain embodiments, each plurality of dimeric probes comprises at least two (e.g., 3, 4, 5, 6, 7, 8, 9, 10) probes.

In certain embodiments, the pluralities of probes hybridize to target nucleic acid sequences in the same pathogen.

In certain embodiments, the pluralities of probes hybridize to target nucleic acid sequences in different pathogens.

In certain embodiments, the array comprises pluralities of dimeric probes that specifically hybridize to target nucleic acid sequences in about two (e.g., about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 or 34) different pathogens (e.g., each plurality of dimeric probes hybridizes to a specific target sequence and each target sequence is particular to a given pathogen). In certain embodiments, the array comprises pluralities of dimeric probes that specifically hybridize to target nucleic acid sequences in about 35 different pathogens. In certain embodiments, the array comprises pluralities of dimeric probes that specifically hybridize to target nucleic acid sequences in about 50 different pathogens. In certain embodiments, the array comprises pluralities of dimeric probes that specifically hybridize to target nucleic acid sequences in about 75 different pathogens. In certain embodiments, the array comprises pluralities of dimeric probes that specifically hybridize to target nucleic acid sequences in about 100 (e.g., about 125, 150, 175, 200, 250, 300, 350, 400, 450, 500, 750, 1,000, 2,000, 3,000, 4,000, 5,000, 10,000, 25,000, 50,000, 75,000, 100,000, 500,000, etc.) different pathogens.

In certain, embodiments, the target nucleic acid sequence is located in an internal transcribed spacer sequence of an rRNA gene. In certain, embodiments, the target nucleic acid sequence is located in EF1-alpha, Beta-tubulin, RPB1, SSU, or LSU.

In certain embodiments, the pluralities of dimeric probes are selected from the sequences listed in Table 2 or Table 7.

In certain embodiments, the pluralities of dimeric probes are selected from SEQ ID NO:4 to SEQ ID NO:9, SEQ ID NO:19 to SEQ ID NO:24, SEQ ID NO:28 to SEQ ID NO:33, SEQ ID NO:42 to SEQ ID NO:45, SEQ ID NO:48 to SEQ ID NO:51, SEQ ID NO:57, SEQ ID NO:58 and SEQ ID NO:73 to SEQ ID NO:301.

In certain embodiments, the pluralities of dimeric probes are selected from SEQ ID NO:4 to SEQ ID NO:6, SEQ ID NO:19 to SEQ ID NO:21, SEQ ID NO:28 to SEQ ID NO:30, SEQ ID NO:42, SEQ ID NO:43, SEQ ID NO:48, SEQ ID NO:49, SEQ ID NO:57, and SEQ ID NO:73 to SEQ ID NO:301.

In certain embodiments, a target sequence is from a fungal, viral, or bacterial pathogen.

In certain embodiments, a target sequence is from a pathogen of turfgrass.

In certain embodiments, a target sequence is from *Brumeria graminis, Bipolaris zeicola, Colletotrichum cereal, Eudarluca caricis, Puccinia coronate, Puccinia persistens* var *triticina, Puccinia striiformis, Puccinia graminis, Puccinia graminis* f. sp. *Tritici, Pythium volutum, Pythium torulosum, Pythium arrhenomanes, Pythium deliense, Pythium rostratifingens, Pythium rostratum, Pythium aphanidermatum, Pythium myriotylum, Pythium arrhenomanes, Rhizoctonia solani, Ceratobasidium cereal, Waitea circinata, Rhizoctonia zeae, Waitea circinata* var. *circinata, Rhizoctonia oryzae, Sclerotinia homoeocarpa, Typhula incarnate, Typhula ishikariensis, Gaeumannomyces graminis, Magnaporthe grisea, Magnaporthe oryzae, Magnaporthe poae, Gaeumannomyces incrustans, Magnaporthe rhizophila, Magnaporthe salvinii, Microdochium bolleyi, Microdochium nivale, Gleocercospora sorghi, Laetisaria fuciformis, Leptosphaeria korrae, Ophiosphaerella herpotricha, Ophiosphaerella agrostis, Limonomyces roseipellis, Acidovorax avenae, Xanthomonas translucens* pv. *Poae, Curvularia trifolii, Trichoderma virens, Urocystis agropyri, Ustilago striiformis, Lycoperdon* spp, *Bovista, Agaricus, Marasmius, Lepiota, Athelia rolfsii, Gibberella zeae, Fusarium solani, Fusarium oxysporum (F. oxysporum), Fusarium* spp, *Poa annua* (RBCL), *Lolium perenne* (RBCL), *Agrostis stolonifera* (RBCL), *Poa annua* (matK), *Poa pratensis* (matK), *Agrostis stolonifera* (matK), *Motierella elongata, Fusarium equisetti* or *Waitea circinata*var. *zeae*.

In certain embodiments, a target sequence is from *Rhizoctonia solani, Pythium aphanidermatum, Fusarium solani* or *F. oxysporum*.

In certain embodiments, the array further comprises at least one positive control probe (e.g., a universal probe or a probe that hybridizes to a target sequence found in a class of pathogens, for example, such as a target sequence found in all fungi and/or oomycetes).

In certain embodiments, the at least one positive control probe is selected from SEQ ID NO:48 to SEQ ID NO:51 and SEQ ID NO:305 to SEQ ID NO:308.

In certain embodiments, the array further comprises at least one negative (i.e., internal) control probe (e.g., a probe that is designed not hybridize to any sequence from a target pathogen, such as, for example, a probe that contains nucleotide mismatches as compared to the positive control probe sequence, for example, two mismatched nucleotides).

In certain embodiments, the at least one negative control probe is selected from SEQ ID NO:57, SEQ ID NO:58, and SEQ ID NO:302 to SEQ ID NO:304.

BRIEF DESCRIPTION OF THE FIGURES

FIG. 2A, Macroarray design. Specific probes for *Pythium aphanidermatum* (Pa), *Rhizoctonia solani* (Rs), *Fusarium solani* (Fs), and *F. oxysporum* (Fo, Fox) were spotted in the four shaded regions. Each of the five types of oligonucleotide probes was spotted in a row as follows: row A, DA; B, dimer; C, monomer; D, M-A10; E, M-A20; F (except F8 spotted with monomer), DA; G (except G8 spotted with M-A10), dimer; H (except H8 spotted with M-A20), monomer. Positive controls were spotted in A1, B1, C1, D1, E1, G1, H1, F8, G8, and H8. Internal controls were spotted in A5, B5, C5, D5 and E5. FIG. 2B, C, D and E show macroarray hybridization results with *P. aphanidermatum, F. solani, R. solani*, and *F. oxysporum*, respectively.

DETAILED DESCRIPTION

Figure 1:
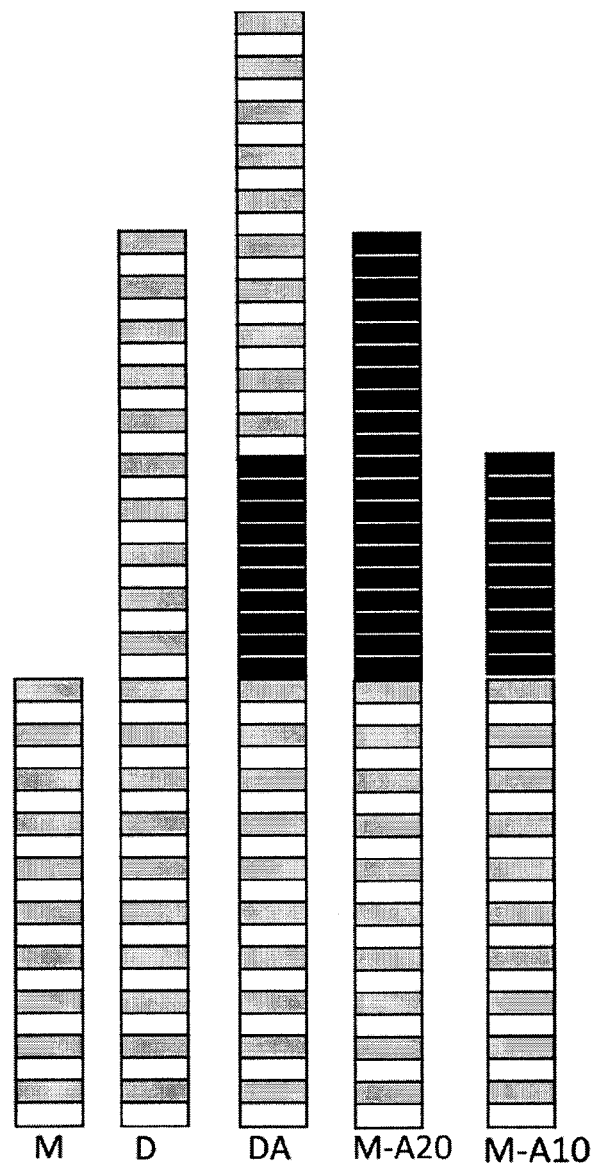
FIG. 1. Schematic representation of the five types of oligonucleotide probes used in the diagnostic macroarray. M=monomer (20-24 nt); D=dimer (40-48 nt); DA=dimer with poly-adenine spacer (black boxes) of 10 bases between the two repeats (50-58 nt); M-A20=monomer with a poly-adenine tail (black boxes) of 20 bases (40-44 nt); and M-A10=monomer with a poly-adenine tail (black boxes) of 10 bases (30-34 nt).

Disease management can be improved with more rapid and more accurate pathogen detection and identification techniques. As described herein, a macroarray diagnostic technique with enhanced detection sensitivity has been developed. The use of repeat sequence probes (dimers) greatly improves the sensitivity of the macroarray. The dimeric probes reliably detected 0.01 fg target genomic DNA, which is lower than the detection limits of most currently available molecular diagnostic methods, such as the conventional PCR and real-time PCR. Dimer probes also had lower signal variability, thereby increasing the macroarray signal uniformity. This technique is useful for early human, animal or plant disease diagnosis, e.g., when only trace amounts of target microbes are present in a sample. The technique can be adapted and applied to microbial ecological studies and other research areas.

Traditionally, plant diagnosticians use direct observations and/or culturing of pathogens from diseased plant samples to make a diagnosis. These methods are often time consuming and insufficient to identify pathogens to the species level. More recent advancements, such as serology and PCR assays, also have their drawbacks. For instance, immunoassay typing with antibodies has been found to be less specific than DNA-based methods. Quantitative PCR (qPCR), a widely used technology in medical, agriculture, and the food industry, offers an alternative detection platform. However, it is limited in terms of throughput where only one or a few pathogens can be detected in a test reaction (van Doorn et al., Appl. Environ. Microbiol., 75, 4185-4193 (2009); Ivnitski et al., Biotechniques 35, 862-869 (2003); Uttamchandani et al., Trends Biotechnol. 27, 53-61 (2009); Lievens et al., FEMS Microbiol. Lett. 223, 113-122 (2003); Lievens et al., Environ. Microbiol. 7, 1698-1710 (2005)). Considering the vast diversity of pathogens, an ideal pathogen detection tool would be characterized by its monitoring capacity for a wide range of pathogen groups as well as by its accuracy and sensitivity (Lee et al., J. Microbiol. Meth. 65, 453-467 (2010)).

DNA diagnostic arrays are another molecular tool that offer a fast, culture-independent alternative for the detection of microbes from field samples (Lievens et al., Phytopathology 95, 1374-1380 (2005); Lievens et al., J. Microbiol. Meth. 80, 76-85; (2010); Zhang et al., Plant Dis. 92, 953-960 (2008); Gilbert et al., J. Cotton Science 12, 165-170 (2008)). The advantage of the array technique is its high throughput compared to other detection methods. Hundreds of different pathogens can be simultaneously detected with one array in one reaction in less than 12 hours. Compared to the glass-based, high-density microarray, the membrane-based macroarray offers a cost-efficient and flexible platform and, therefore has been adopted by many disease diagnosis development projects (Maoka et al., Plant Dis. 94, 1248-1254 (2010)). Moreover, macroarray results can be visualized with an unaided eye, which offers simplicity compared to microarrays. Recently, the application of chromogenic technology in macroarrays has further increased their versatility for use in laboratories or diagnostic labs with limited resources (Abdullahi et al., J. Virol. Methods 160, 90-100 (2009)).

Like other DNA diagnostic array technologies, macroarrays combine the advantage of two molecular biological advancements. First, the growing amount of DNA sequences available in publicly accessible databases (e.g., GenBank) allows for creation of signature probes specific to a species or infra-species target. Second, the high throughput capacity of the array technology permits hundreds of DNA oligomers to be queried simultaneously and produces signals indicative of matches between the oligomer and the query. The macroarray technique has been applied in a variety of areas. For example, in human biology it has been used for identification of different mRNA species present in human ejaculated spermatozoa (Dadoune et al., Mol. Hum. Reprod. 11, 133-140 (2004)) and in diagnosing ovarian cancer in epithelial cells (Chatterjee et al., Cancer Res. 66, 1181-1190 (2006)); while in veterinary science, macroarrays have been used for monitoring the Crimean-Congo Hemorrhagic fever virus, a tickborne zoonotic virus found across Africa, Eastern Europe and Asia (Wolfel et al., J. Clin. Microbiol. 47, 1025-1030 (2009)). In plant pathology, membrane-based DNA arrays have been used for detection, identification, monitoring and quantification of phytopathogenic agents (Fessehaie et al., Phytopathology 93, 262-269 (2003); Sholberg et al., Plant Dis. 89, 1143-1150 (2005)), such as phytopathogenic bacteria on potato, pathogens of apples, and pathogenic viruses and fungi in different host plants. At the infra-species level, DNA diagnostic arrays have been used for identification of races and biotypes of *Fusarium oxysporum* f. sp. *vasinfectum* on cotton and the detection of members of the *F. solani* species complex in solanaceous crops (Zhang et al., Plant Dis. 91, 1612-1620 (2007)).

Probe design is the first step in the development of a diagnostic array. Parameters such as probe length and annealing temperatures (or GC content) play a role in array performance that have great impact on the fidelity of the assay, particularly with regard to the level of specificity and sensitivity attained (Barad et al., Genome Res. 14, 2486-2494 (2004); Goff et al., RNA Biology 2, E9-E16 (2005); Loy et al., Clin. Chim. Acta 363, 106-119 (2006)). If probes are not optimized for specificity, arrays may generate false positives due to cross-hybridization to similar sequences. On the other hand, high stringency often results in reduced signal intensity and may lead to false negatives. The occurrence of false positives and negatives is problematic because it is difficult to envisage whether a probe will attach efficiently to its target sequence and yield a good hybridization signal based on the sequence information alone (Li et al., Bioinformatics 17, 1067-1076 (2001); Chou et al., Nucleic Acids Res. 32, e99 (2004)). The design of effective probes is a challenge especially in related species where there is a high degree of sequence similarities. Scientists have therefore resulted to engineering redundancy into the DNA array's systems to improve accuracy and analytical power simply by over-representation. That is, using multiple probes per target to achieve reliable and accurate detection.

A number of studies have been able to achieve high levels of specificity with DNA arrays, but sensitivity has remained elusive (Wong et al., Genome Biol. 8, R93 (2007)), which made it difficult to detect species that were present at very low concentrations.

Increasing probe length can increase the array sensitivity, but specificity is often sacrificed. However, the impact of doubling (dimer) or tripling (trimer) a short probe sequence (about 20 nt monomer) to maintain the array specificity has not been addressed.

The objectives of this study were to develop a novel technical approach that could increase the sensitivity of a macroarray to enhance its early pathogen detection power, and which could maintain the macroarray detection specificity to ensure accurate pathogen identification. In this study, we designed and compared the performance of monomers, monomers with a ten-adenine tail (M-A10), monomers with 20 adenine tail (M-A20), dimers, and dimers with a ten-adenine spacer (DA), using a membrane-based macroarray platform (FIG. 1). It was hypothesized that (1) Dimeric oligonucleotide probes would be more sensitive than monomeric probes, (2) Poly-A spacer and tails would increase sensitivity of the probes, and that (3) Monomeric and dimeric probes would have equal specificity. Probes tested in this study were based on four important microbial pathogens of cereals, turfgrass and other plants—*Rhizoctonia solani* (basidiomycete), *Pythium aphanidermatum* (oomycete), *Fusarium solani* (ascomycete) and *F. oxysporum* (ascomycete) that cause brown patch, Pythium blight, root and vascular diseases, respectively.

Rapid and early diagnosis of microbe-causing diseases requires a technique capable of detecting low quantity of causal agents from the natural host environment. Accordingly, described herein is an improved macroarray detection technique that provides enhanced and consistent signals of detection with small reductions in specificity. The tandem-repeat dimeric probes (40-48 nt) had significantly higher sensitivity and lower signal variability compared to the monomers (20-24 nt).

The diagnostic array technique for microbe detection demands both high sensitivity and specificity. While developing macroarrays for the detection of solanaceous plant pathogens, Zhang et al. (2007) optimized the hybridization temperature to reduce cross-hybridization. However, this improvement in specificity came with a considerable sacrifice in signal intensity, which is also determined by the probe length. Long sequence probes can decrease the array specificity. The hypothesis that dimeric probes containing two short identical sequences would enhance the DNA array sensitivity without sacrificing the specificity was tested. However, two monomers in tandem might interfere with hybridization of targets to the two matching sequences. Thus, the possibility that addition of a spacer in between may facilitate the binding of long target DNA fragments to the probes without unnecessary tangling was tested. However, the results showed that overall, dimers with poly-A spacer did not produce stronger signals than the dimers. This suggests that the proximity of two monomers to each other does not have a significant effect on hybridization. Previous work has shown that addition of spacers can have a large effect on hybridization signals for 15-30 mer oligonucleotide probes (Shchepinov et al., Nucleic Acids Res. 25, 1155-1161 (1997); Southern et al., Nature Genet., 21, 5-9 (1999); Guo et al., Nat. Biotechnol. 15, 331-335 (1997)).

To assess the reproducibility of the results, eleven sets of probes for DA, D, and M types (two to three independent sets for each of the four species) in addition to the controls were examined in this study. For the diagnostic arrays, multiple probes for each target species also ensures positive detection of genetically diverse target species. Random signal variation (noise) and the systematic deviation of the measurement from the true signal due to probe specific or other confounding technical effects can interfere with the results. Signal variation, expressed as a coefficient of variation (CV), showed that dimer probes had lowest variation while the monomers showed wide variability. Based on the statistical principles of sampling, the smaller the CV for the hybridization signals, the more reliable or reproducible the results are (Chou et al., 2004). This implies that fewer probes are needed when using dimer probes.

Although dimeric probes provided a low measurement variation and superior signal intensity, some dimeric probes tested here were relatively poor in discriminating sequences with high level of similarity (especially 1 nt differences). Cross-homology is a predicator of cross-hybridization. The concept of using dimers as probes does not change the level of similarity compared to the monomers. Therefore, the cross-hybridization observed maybe a consequence of other factors such as the binding energy accruing from longer probes. Longer probes typically have higher binding energy than shorter probes. Cross-hybridization observed here was only limited to members of the same genus and occurred in highly similar sequences where the mismatch base was located near the end or in a chain of the same base. This should be preventable in future array probe designs by avoiding such regions of a gene. These results showed that in all cases, the dimeric probes were able to distinguish strains that differed from the target by 3 or more nucleotides. Full discrimination also achieved for most cases of 2-nucleotide mismatches and one case of single nucleotide match. Therefore, with improved probe design strategy as described, the dimer array system is expected to distinguish between closely related pathogens, at species and infra species levels, such as race and subspecies.

Even though this macroarray system displayed some false-positives, it was remarkable in detecting low quantities of pathogen DNA. The dimer probes were able to detect as low as 0.1 pg target DNA in raw or mixed biological samples with plant extract despite the possibility of PCR bias in amplification. The dimers also reliably detected 0.01 fg target DNA from pure cultures on the array, while gel electrophoresis required a thousand fold more DNA for a positive detection. Assessment of low concentrations of target DNA that is only present in few plant cells can be very elusive. Understanding pathogen biology is of paramount importance in disease diagnosis, since some pathogens are localized in certain parts of the tissue, while others are systemic in nature or cause symptoms in advance of tissue pathogen ingress. Visualization of pathogen structures using dissecting microscope to locate tissue with signs of the disease followed by targeted isolation of DNA from these tissues may improve the power of molecular detection.

In summary, reported herein is the finding that dimeric probes (e.g., 40-48 nt) enhance macroarray performance. The optimized dimer macroarray system demonstrated significantly higher sensitivity and consistency than the conventional monomer oligonucleotide arrays. Its detection sensitivity is also higher than many other currently available molecular diagnostic methods, such as PCR and real-time PCR. Moreover, this method is faster (less than 12 hours) than the traditional culture-based diagnostic method, which often takes days or even weeks. Therefore, this technique should be useful for early disease diagnosis when only trace amounts of target microbes are present in a sample. These findings should aid in the development of a multiplex diagnostic macroarray system to facilitate early disease diagnosis and management. The technique also can be adapted and applied to microbial ecological studies and other research areas.

The term "nucleic acid" refers to deoxyribonucleotides or ribonucleotides and polymers thereof in either single- or double-stranded form, made of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The term "nucleotide sequence" refers to a polymer of DNA or RNA which can be single-stranded or double-stranded, optionally containing synthetic, non-natural or altered nucleotide bases capable of incorporation into DNA or RNA polymers. The terms "nucleic acid," "nucleic acid molecule," or "polynucleotide" are used interchangeably.

Certain embodiments of the invention encompass isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

The following terms are used to describe the sequence relationships between two or more nucleotide sequences: (a)

"reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm. Non-limiting examples of such mathematical algorithms are the algorithm of Myers and Miller (Myers and Miller, CABIOS, 4, 11 (1988)); the local homology algorithm of Smith et al. (Smith et al., Adv. Appl. Math., 2, 482 (1981)); the homology alignment algorithm of Needleman and Wunsch (Needleman and Wunsch, JMB, 48, 443 (1970)); the search-for-similarity-method of Pearson and Lipman (Pearson and Lipman, Proc. Natl. Acad. Sci. USA, 85, 2444 (1988)); the algorithm of Karlin and Altschul (Karlin and Altschul, Proc. Natl. Acad. Sci. USA, 87, 2264 (1990)), modified as in Karlin and Altschul (Karlin and Altschul, Proc. Natl. Acad. Sci. USA 90, 5873 (1993)).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (Higgins et al., CABIOS, 5, 151 (1989)); Corpet et al. (Corpet et al., Nucl. Acids Res., 16, 10881 (1988)); Huang et al. (Huang et al., CABIOS, 8, 155 (1992)); and Pearson et al. (Pearson et al., Meth. Mol. Biol., 24, 307 (1994)). The ALIGN program is based on the algorithm of Myers and Miller, supra. The BLAST programs of Altschul et al. (Altschul et al., JMB, 215, 403 (1990)) are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

For purposes of the present invention, comparison of nucleotide sequences for determination of percent sequence identity to the promoter sequences disclosed herein may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, 80%, 90%, or even at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even 95%, 96%, 97%, 98% or 99%, sequence identity to the reference sequence over a specified comparison window. In certain embodiments, optimal alignment is conducted using the homology alignment algorithm of Needleman and Wunsch (Needleman and Wunsch, JMB, 48, 443 (1970)). An indication that two peptide sequences are substantially identical is that one peptide is immunologically reactive with antibodies raised against the second peptide. Thus, a peptide is substantially identical to a second peptide, for example, where the two peptides differ only by a conservative substitution. Thus, certain embodiments of the invention provide nucleic acid molecules that are substantially identical to the nucleic acid molecules described herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point (Tm) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m$ 81.5° C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), the SSC concentration is increased so that a higher temperature can be used. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. For short nucleotide sequences (e.g., about 10 to 50 nucleotides), stringent conditions typically involve salt concentrations of less than about 1.5 M, less than about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids that have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

In addition to the chemical optimization of stringency conditions, analytical models and algorithms can be applied to hybridization data-sets (e.g. microarray data) to improve stringency.

Certain embodiments of the invention will now be illustrated by the following non-limiting Examples.

EXAMPLE 1

Dimeric Oligonucleotide Probes Enhance Diagnostic Macroarray Performance

Disease management would be improved with more rapid and more accurate pathogen detection and identification techniques. Described herein is a macroarray diagnostic technique with enhanced detection sensitivity with only small reduction in specificity. With probes designed based on the internal transcribed spacer sequences of the rRNA genes of fungal and oomycete strains, a macroarray was produced that included five types of oligonucleotide probes: monomers (20-24 nt), dimers (40-48 nt), dimers with a poly-A spacer of 10 bases between the two repeats (50-58 nt), monomers with a poly-A tail of 10 (30-34 nt) and 20 (40-44 nt) bases. The use of repeat sequence probes (dimers) greatly improved the sensitivity of the macroarray. The dimeric probes could reliably detect 0.01 fg target genomic DNA, which is lower than the detection limits of most currently available molecular diagnostic methods, such as the conventional PCR and real-time PCR. Dimer probes also had lower signal variability, thereby increasing the macroarray signal uniformity. However, in a few cases, specificity was reduced in the dimer probes. Cross-hybridization occurred in highly similar sequences where the mismatched base was located near the end or in a chain of the same base, but this should be prevented in future array probe design.

Probe Sensitivity

Figure 3:
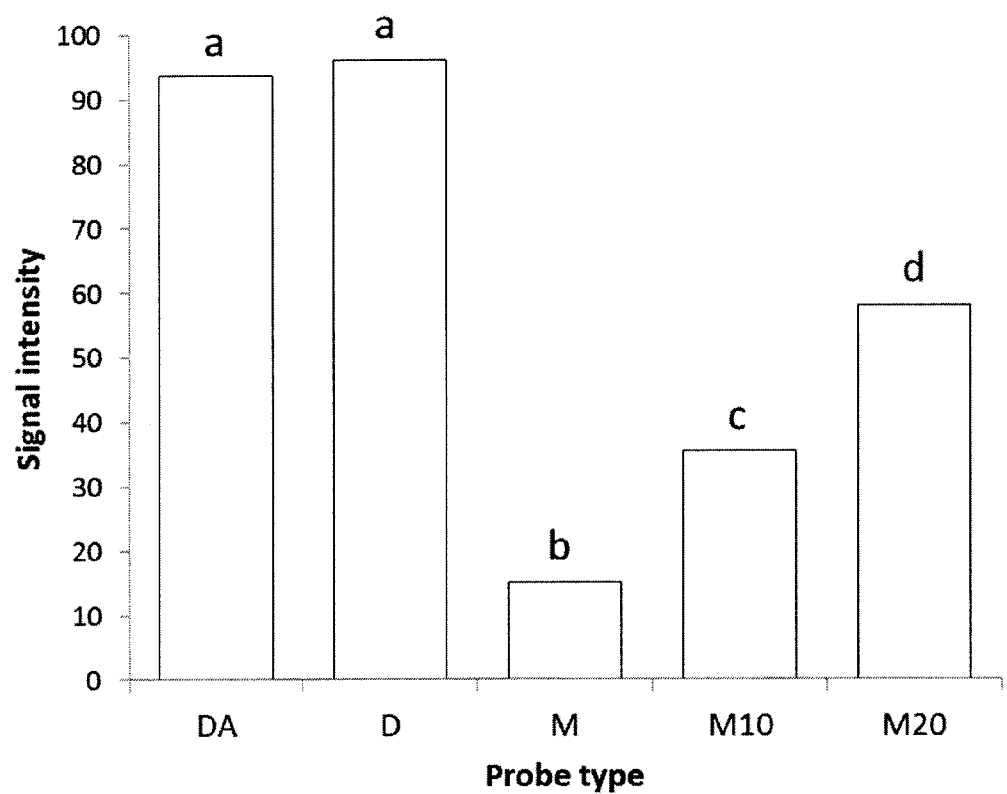
FIG. 3. Signal intensity comparison of different oligonucleotide probe types. Y-axis represents the mean signal intensity levels as measured with inverted grayscale values. For each probe type (X-axis), there are three independent probes targeting each species (four species tested) except for *F. oxysporum* which had two probes per probe type, making a total of 11 unique probes for M, D and DA oligonucleotide probe types. Only two species (6 unique probes) were tested for M-A10 and M-A20 probe types. Two isolates were tested for each species except for *F. oxysporum*, which had only one isolate available. The experiment was conducted twice. Means with the same letter do not differ significantly (Tukey test, $P<0.05$, $n=11$ for M, D, and DA whereas $n=6$ for M-A10 and M-A20).

Dimers and DA had significantly higher sensitivity than those of the M, M-A10 and M-A20 (FIG. 3). To test whether the monomers were being outcompeted in the race for hybridization targets, monomers were printed on a separate membrane. Results showed that there was no significant difference in signal intensities between monomers printed on a separate array and monomers printed in same array with dimers (Table 5).

Signal Uniformity

Figure 2:
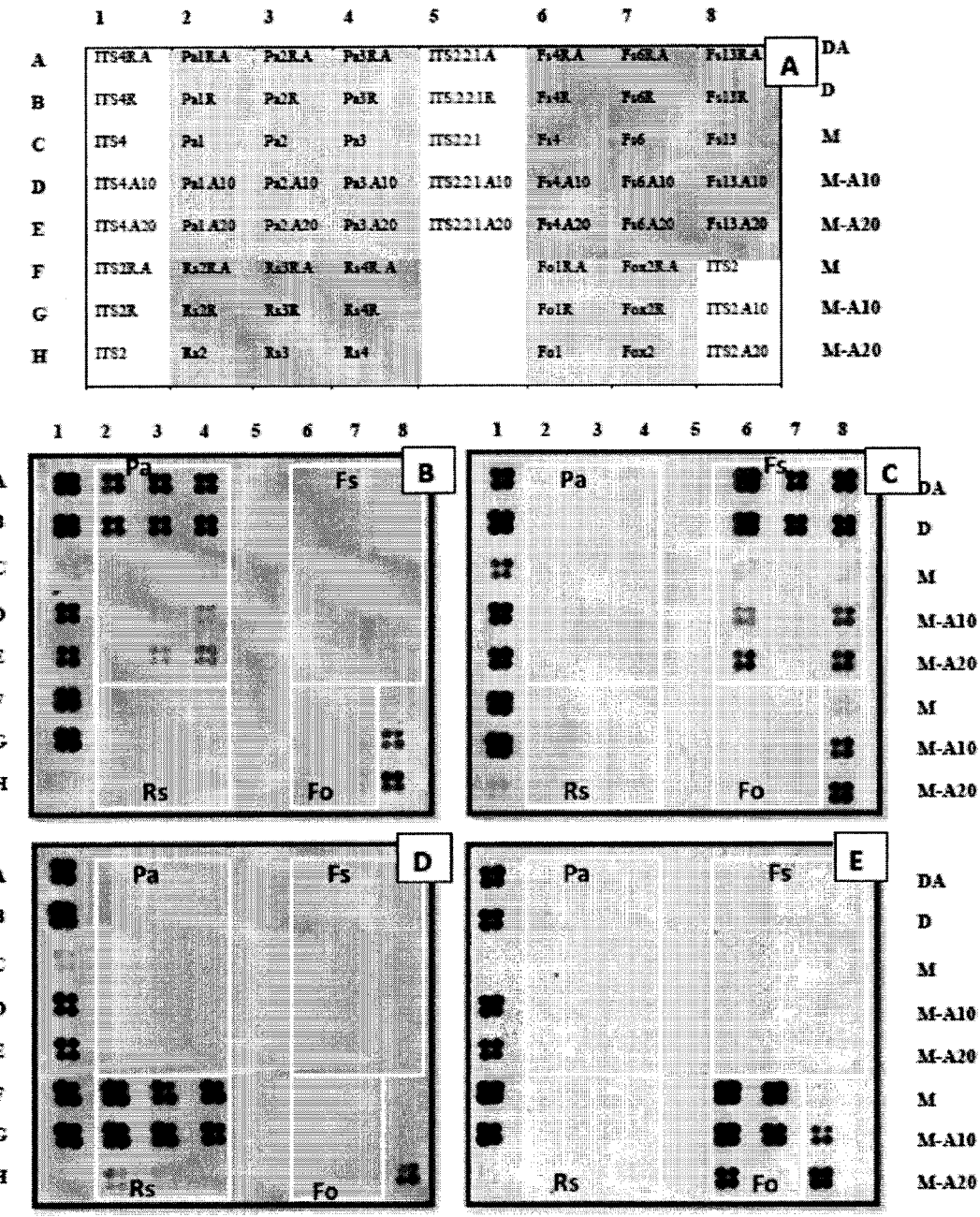
FIG. 2. Macroarray design and hybridization results.
Figure 4:
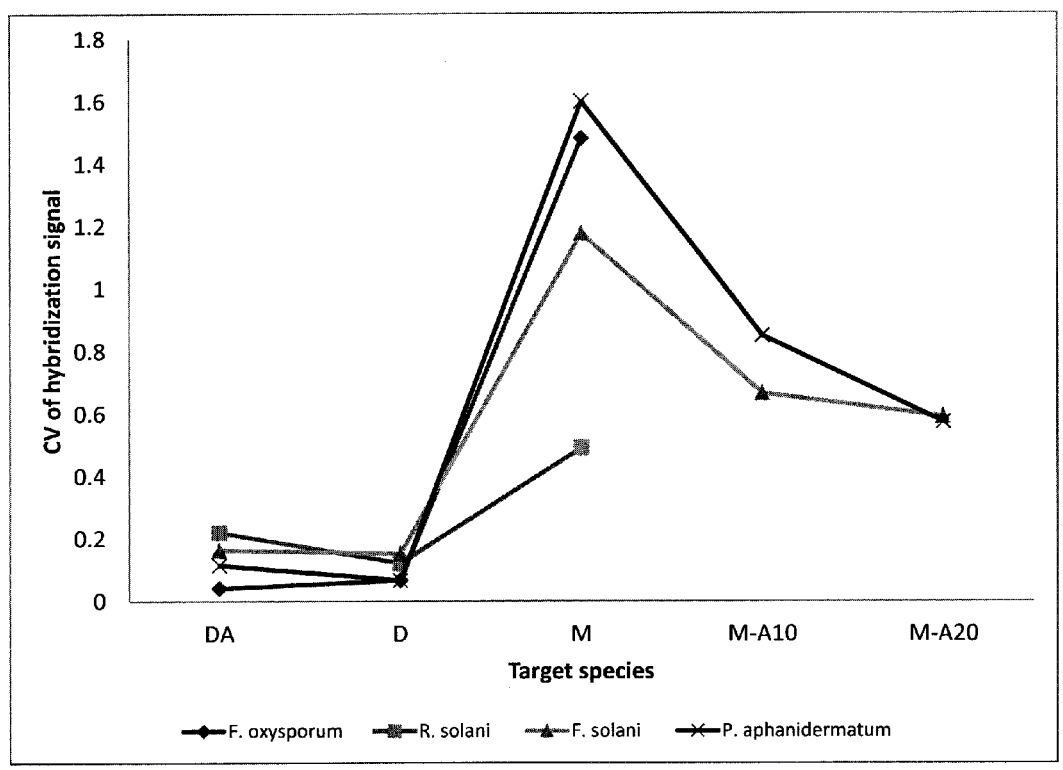
FIG. 4. Coefficient of variation of hybridization signal intensity among different probe types for the four target species. The coefficient of variation (CV), is defined as the standard deviation divided by the means of the hybridization signals and is used here as a measure of the variation of signal intensity.

Signal intensities of monomeric probes were most variable compared to the other types of probes (FIG. 2, FIG. 4). The signal intensities for monomers were so diverse that $F.$ oxysporum had one probe with an inverted gray value of 89 while the other was showing only 4. On the same array, dimers and dimers with poly-A spacer derived from those monomers had lesser inverted gray value disparity (117-108 and 117-114, respectively). The coefficient of variation (CV), defined here as the standard deviation divided by the means of the hybridization signals was used as a measure of the variation of signal intensity (Chou et al., 2004; FIG. 4). Overall, the dimers displayed the lowest variability, followed by the dimers with poly-A and then the monomers M-A20 and M-A10. Monomers alone had the greatest variability.

Limit of Detection and Validation

Figure 5:
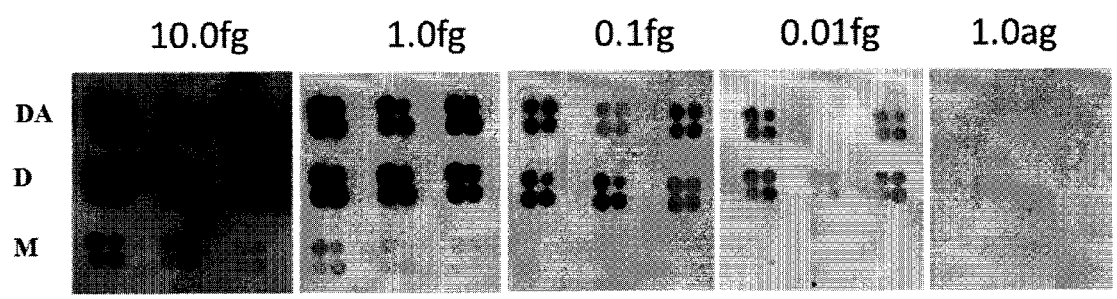
FIG. 5. Macroarray results when probes were hybridized with amplified *Rhizoctonia solani* from 10× serial diluted genomic DNA (10 fg to 1 ag).

The dimer probes could reliably detect up to 0.01 fg genomic DNA, which is a thousand times lower than using PCR product visualization with gel electrophoresis (FIG. 5). A simulation based on a condition where the pathogen DNA was serially diluted while holding the host grass DNA at 1 ng showed that dimeric probes could detect target DNA at all levels tested (Table 3), including 0.1 pg at a ratio of $1:10^4$ pathogen to host DNA for $R.$ solani and $P.$ aphanidermatum. Mixing the DNA of the target species, commonly found co-inhabiting fungal species and the host plant did not interfere with the hybridization reactions for all reactions tested (Table 3). The macroarray was also successfully validated with target species infected plant or soil materials. The array detection and identification results matched with the identification based on traditional microscopic observation, culture isolation and ITS DNA sequence (Table 1).

Array Specificity

There was no cross hybridization to $P.$ aphanidermatum and $R.$ solani probes from any of the non-target isolates. Cross-hybridization was observed in three sets of dimers and DA probes (Table 6) when reacting with non-target species that had one or two nucleotide sequence mismatches (Table 4). The mismatches between the cross-hybridized probes and the corresponding non-target sequences were located either in chain of A or G ($F.$ solani #F19/probe Fs6 and $F.$ equiseti #S2/probe Fo1, Tables 4) or near the end of the probe sequence ($F.$ solani #F3/probe Fs13). The cross-hybridization signal intensity values were 44% or lower compared to the perfect-match signals. False negatives were only observed in a monomer probe for $P.$ aphanidermatum (Table 6).

Materials and Methods

Isolates

Test isolates used in this study are listed in Table 1. The identity of the target species, $P.$ aphanidermatum and $R.$ solani, was confirmed by morphology and the internal transcribed spacer sequences of the rRNA genes (ITS), while the *Fusarium* species were characterized in another study by partial sequences of translation elongation factor-1α (EF-1α), ITS, and β-tubulin (TUB) genes. In addition, non-target species of *Pythium*, *Rhizoctonia*, and *Fusarium* were used to test the array specificity. Three common co-inhabiting fungi in turfgrass soil, *Curvularia trifolii*, *Trichoderma vixens*, and *Mortierella elongata* were also included in the study for validation and cross-reaction tests.

200 μM each of the dNTPs, 0.5 μM of each forward and reverse primers, and 0.5 U Taq polymerase. The thermal cycling parameters were 95° C. for 5 min; 35 cycles of 95° C. for 1 min, 56° C. for 1 min., and 72° C. for 1 min; followed by 10 min at 72° C. PCR products were purified according to the manufacturer's protocol using the QIAquick PCR Purification Kit (Qiagen), quantified using NanoVue spectrophotometer and sequenced when identity of the isolates needed to be confirmed. Sequencing of the purified ITS PCR products was

TABLE 1

Microbial, host species and substrate used for testing and validating the macroarray in this study

| Microbial/host species | Collection ID | Host/substrate | Origin | GenBank accession |
|---|---|---|---|---|
| Fungi-Zygomycota | | | | |
| *Mortierella elongata* | #141 | *Poa annua* | Denville, NJ | — |
| Fungi-Ascomycota | | | | |
| *Curvularia trifolii* | #185 | *Agrostis* sp. | New Brunswick, NJ | — |
| *Fusarium equisetti* | #S2 | turfgrass soil | New Brunswick, NJ | — |
| *F. oxysporum* | #F2 (NRRL 54168) | *Lilium longiflorum* bulbs | New Brunswick, NJ | HQ379648 |
| *F. oxysporum* | #S4 | turfgrass soil | New Brunswick, NJ | — |
| *F. solani* | #F3 (NRRL 54169) | *Lilium longiflorum* bulbs | New Brunswick, NJ | HQ379661 |
| *F. solani* | #F19 (NRRL 54185) | *Lilium longiflorum* bulbs | New Brunswick, NJ | HQ379663 |
| *Trichoderma virens* | #126-L | *Agrostis stolonifera* | New Brunswick, NJ | — |
| Fungi-Basidiomycota | | | | |
| *Rhizoctonia solani* | #RH 20 | unknown | State College, PA | — |
| *R. solani* | #98 | *Lolium multiflorum* | New Brunswick, NJ | — |
| *Waitea circinata* var. *circinata* | #10 | *Agrostis* sp. | NJ | — |
| *W. circinata* var. *circinata* | #158 | *Agrostis* sp./*Poa* sp. | Bedminster, NJ | HQ166071 |
| *W. circinata* var. *zeae* | #1 | *Poa annua* | New Brunswick, NJ | — |
| Stramenopiles-Oomycota | | | | |
| *Pythium aphanidermatum* | #60 | *Festuca arundinacea* | NJ | — |
| *P. aphanidermatum* | #99 | *Lolium multiflorum* | New Brunswick, NJ | — |
| *P. rostrum* | #123p | *Agrostis* sp. | New Brunswick, NJ | — |
| *P. torulosum* | #122 | *Poa annua* | New Brunswick, NJ | — |
| *P. volutum* | #124p-1 | *poa annua* | New Brunswick, NJ | — |
| Host/substrate | | | | |
| —[a] | #199 | *Agrostis stolonifera* | New Brunswick, NJ | — |
| —[b] | NA | *Poa annua* | New Brunswick, NJ | — |
| —[c] | #176 | *Poa annua* | New Brunswick, NJ | — |
| —[d] | NA | Soil | New Brunswick, NJ | — |

NRRL = Agricultural Research Service Culture Collection (NCAUR, Peoria, IL).
[a]*Agrostis stolonifera* with symptoms of brown patch.
[b]Asymptomatic, disease free *Poa annua* from greenhouse.
[c]*Poa annua* with symptoms of *Pythium* blight.
Soil substrates used were those associated with *P. aphanidermatum* and *R. solani*.
NA = Not available.

DNA Extraction, Amplification, Purification and Sequencing

Genomic DNA from all microbial isolates was extracted from 1- to 2-week-old cultures growing on PDA plates (Difco laboratories, Detroit, Mich.) using the UltraClean Soil DNA kit (MoBio Laboratories Inc., Solana Beach, Calif., USA) or DNeasy Plant Mini kit (Qiagen Inc., Valencia, Calif., USA), following the manufacturer's protocol. The extracted genomic DNA was quantified using a NanoVue spectrophotometer (GE Healthcare Bio-Sciences Corp., Piscataway, N.J., USA) and diluted to 5 ng/μl before PCR. The ITS region was amplified with primers ITS1 and ITS4 (White et al., In: Innis et al. (Eds.), PCR Protocols: A Guide to Methods and Applications. Academic Press, New York, pp. 315-322 (1990)). PCR was carried out in a 25 μl reaction volume containing 3 μl (15 ng) genomic DNA, 1×PCR buffer (Applied Biosystems, Foster City, Calif., USA), 1.5 mM MgCl$_2$, run on an Applied Biosystems 3730xl sequencer by GENEWIZ (GENEWIZ, Inc., South Plainfield, N.J., USA).

Oligonucleotide Probe Design and Array Development

Two sets of probes, dimers and dimers with a poly-A10 spacer of 10 bases for the four target species and the controls (Table 2) were designed based in part on 20-24 nt oligomer probes previously designed and validated by Lievens et al. (2003), Saiki et al., Proc. Natl. Acad. Sci. USA 86, 6230-6234. (1989), and Zhang et al., (2007, 2008). Accordingly, certain embodiments of the invention are directed to these probes. M-A10 and M-A20 were designed for *P. aphanidermatum* and *F. solani* only (Table 2), since we were more interested with the effect of duplexing but at the same time we wanted to disqualify sequence length as the only factor contributing to the enhanced sensitivity. The performance of the macroarray that contained the five types of probes was tested against the macroarray that contained only the monomeric probes.

The macroarray development followed the procedure described by Zhang et al. (2007). Briefly, 20 μmol of each detector oligonucleotide probe was spotted onto Hybond N+ nylon membranes (GE Healthcare Bio-Sciences Corp., Piscataway, N.J., USA) in quadruplicate using a 96-pin tool (V&P Scientific Inc., San Diego, Calif., USA). Three types of controls were also spotted. First, the positive controls included the ITS4 primer, which is a universal primer for both fungi and oomycetes, and ITS2, which is a fungal universal primer (Table 2). Second, internal controls that differed from ITS2 at two bases were also spotted on the membrane. Negative controls were sterile water and the spotting buffer. The positive and internal controls also constituted dimers, DA, M-A10 and M-A20. The spotted membranes were air dried for 10 min and then fixed by UV exposure at 240 mJ/cm$^2$. After incubation in a 0.5% sodium dodecyl sulfate (SDS) solution at 60° C. for an hour, membranes were rinsed in 100 mM Tris (pH 8.0) for 5 min, and kept moist at 4° C. until used. This last step was also used for stripping the array.

TABLE 2

Probe name, type, sequence, length and targeted species used in this study.

| Probe name | Probe type[a] | Probe sequence | Reference[b] | Probe Length | Probe target |
|---|---|---|---|---|---|
| Specific target probe | | | | | |
| Pa1 | M | GGAGAGAGATGGCAGAATGTGAG (SEQ ID NO: 1) | Saiki et al. 1989 | 23 | P. aphanidermatum |
| Pa2 | M | GGGAGAGAGATGGCAGAATGTGAG (SEQ ID NO: 2) | Saiki et al. 1989 | 24 | P. aphanidermatum |
| Pa3 | M | GAGGTGTACCTGAATTGTGTGAGG (SEQ ID NO: 3) | Saiki et al. 1989 | 24 | P. aphanidermatum |
| Pa1R | D | GGAGAGAGATGGCAGAATGTGAGGGAGAGAGATGGCAGAATGTGAG (SEQ ID NO: 4) | | 46 | P. aphanidermatum |
| Pa2R | D | GGGAGAGAGATGGCAGAATGTGAGGGGAGAGAGATGGCAGAATGTGAG (SEQ ID NO: 5) | | 48 | P. aphanidermatum |
| Pa3R | D | GAGGTGTACCTGAATTGTGTGAGGGAGGTGTACCTGAATTGTGTGAGG (SEQ ID NO: 6) | | 48 | P. aphanidermatum |
| Pa1R-A | DA | GGAGAGAGATGGCAGAATGTGAGAAAAAAAAAAGGAGAGAGATGGCAGAATGTGAG (SEQ ID NO: 7) | | 56 | P. aphanidermatum |
| Pa2R-A | DA | GGGAGAGAGATGGCAGAATGTGAGAAAAAAAAAAGGGAGAGAGATGGCAGAATGTGAG (SEQ ID NO: 8) | | 58 | P. aphanidermatum |
| Pa3R-A | DA | GAGGTGTACCTGAATTGTGTGAGGAAAAAAAAAAGAGGTGTACCTGAATTGTGTGAGG (SEQ ID NO: 9) | | 58 | P. aphanidermatum |
| Pa1-A10 | M-A10 | GGAGAGAGATGGCAGAATGTGAGAAAAAAAAAA (SEQ ID NO: 10) | | 33 | P. aphanidermatum |
| Pa2-A10 | M-A10 | GGGAGAGAGATGGCAGAATGTGAGAAAAAAAAAA (SEQ ID NO: 11) | | 34 | P. aphanidermatum |
| Pa3-A10 | M-A10 | GAGGTGTACCTGAATTGTGTGAGGAAAAAAAAAA (SEQ ID NO: 12) | | 34 | P. aphanidermatum |
| Pa1-A20 | M-A20 | GGAGAGAGATGGCAGAATGTGAGAAAAAAAAAAAAAAAAAAAA (SEQ ID NO: 13) | | 43 | P. aphanidermatum |
| Pa1-A20 | M-A20 | GGGAGAGAGATGGCAGAATGTGAGAAAAAAAAAAAAAAAAAAAA (SEQ ID NO: 14) | | 44 | P. aphanidermatum |
| Pa3-A20 | M-A20 | GAGGTGTACCTGAATTGTGTGAGGAAAAAAAAAAAAAAAAAAAA (SEQ ID NO: 15) | | 44 | P. aphanidermatum |
| Rs2 | M | CAGTGTTATGCTTGGTTCCACTC (SEQ ID NO: 16) | Zhang et al. 2008 | 23 | R solani |
| Rs3 | M | TGTTGAAACTTAGTATTAGATGCGT (SEQ ID NO: 17) | Zhang et al. 2008 | 23 | R. solani |
| Rs4 | M | GAGTGGAACCAAGCATAACACTG (SEQ ID NO: 18) | Zhang et al. 2008 | 23 | R. solani |

TABLE 2-continued

Probe name, type, sequence, length and targeted species used in this study.

| Probe name | Probe type[a] | Probe sequence | Reference[b] | Probe Length | Probe target |
|---|---|---|---|---|---|
| Rs2R | D | CAGTGTTATGCTTGGTTCCACTCCAGTGTTATGCTTGGTTCCACTC (SEQ ID NO: 19) | | 46 | *R. solani* |
| Rs3R | D | TGTTGAAACTTAGTATTAGATGCGTTGTTGAAACTTAGTATTAGATGCGT (SEQ ID NO: 20) | | 46 | *R. solani* |
| Rs4R | D | GAGTGGAACCAAGCATAACACTGGAGTGGAACCAAGCATAACACTG (SEQ ID NO: 21) | | 46 | *R. solani* |
| Rs2R-A | DA | CAGTGTTATGCTTGGTTCCACTCAAAAAAAAAACAGTGTTATGCTTGGTTCCACTC (SEQ ID NO: 22) | | 56 | *R. solani* |
| Rs3R-A | DA | TGTTGAAACTTAGTATTAGATGCGTAAAAAAAAAATGTTGAAACTTAGTATTAGATGCGT (SEQ ID NO: 23) | | 56 | *R. solani* |
| Rs4R-A | DA | GAGTGGAACCAAGCATAACACTGAAAAAAAAAAGAGTGGAACCAAGCATAACACTG (SEQ ID NO: 24) | | 56 | *R. solani* |
| Fs4 | M | TCGCGTAGTAGCTAACACCTCGC (SEQ ID NO: 25) | Zhang et al. 2007 | 23 | *F. solani* |
| Fs6 | M | CCTGTGAACATACCTAAACGTTG (SEQ ID NO: 26) | Zhang et al. 2007 | 23 | *F. solani* |
| Fs13 | M | TTATACAACTCATCAACCCTGTGA (SEQ ID NO: 27) | Zhang et al. 2007 | 24 | *F. solani* |
| Fs4R | D | TCGCGTAGTAGCTAACACCTCGCTCGCGTAGTAGCTAACACCTCGC (SEQ ID NO: 28) | | 46 | *F. solani* |
| Fs6R | D | CCTGTGAACATACCTAAACGTTGCCTGTGAACATACCTAAACGTTG (SEQ ID NO: 29) | | 46 | *F solani* |
| Fs13R | D | TTATACAACTCATCAACCCTGTGATTATACAACTCATCAACCCTGTGA (SEQ ID NO: 30) | | 48 | *F. solani* |
| Fs4R-A | DA | TCGCGTAGTAGCTAACACCTCGCAAAAAAAAAATCGCGTAGTAGCTAACACCTCGC (SEQ ID NO: 31) | | 56 | *F. solani* |
| Fs6R-A | DA | CCTGTGAACATACCTAAACGTTGAAAAAAAAAACCTGTGAACATACCTAAACGTTG (SEQ ID NO: 32) | | 56 | *F. solani* |
| Fs13R-A | DA | TTATACAACTCATCAACCCTGTGAAAAAAAAAAATTATACAACTCATCAACCCTGTGA (SEQ ID NO: 33) | | 58 | *F. solani* |
| Fs4-A10 | M-A10 | TCGCGTAGTAGCTAACACCTCGCAAAAAAAAAA (SEQ ID NO: 34) | | 33 | *F. solani* |
| Fs6-A10 | M-A10 | CCTGTGAACATACCTAAACGTTGAAAAAAAAAA (SEQ ID NO: 35) | | 33 | *F. solani* |
| Fs13-A10 | M-A10 | TTATACAACTCATCAACCCTGTGAAAAAAAAAA (SEQ ID NO: 36) | | 34 | *F solani* |
| Fs4-A20 | M-A20 | TCGCGTAGTAGCTAACACCTCGCAAAAAAAAAAAAAAAAAAAA (SEQ ID NO: 37) | | 43 | *F. solani* |
| Fs6-A20 | M-A20 | CCTGTGAACATACCTAAACGTTGAAAAAAAAAAAAAAAAAAAA (SEQ ID NO: 38) | | 43 | *F. solani* |
| Fs13-A20 | M-A20 | TTATACAACTCATCAACCCTGTGAAAAAAAAAAAAAAAAAAAA (SEQ ID NO: 39) | | 44 | *F. solani* |
| Fo1 | M | CGTTCCTCAAATTGATTGGCGGTC (SEQ ID N0: 40) | Zhang et al. 2008 | 24 | *F. oxysporum* |

TABLE 2-continued

Probe name, type, sequence, length and targeted species used in this study.

| Probe name | Probe type[a] | Probe sequence | Reference[b] | Probe Length | Probe target |
|---|---|---|---|---|---|
| Fox2 | M | GTTGGGACTCGCGTTAATTCG<br>(SEQ ID NO: 41) | Lievens et al. 2003 | 21 | *F. oxysporum* |
| Fo1R | D | CGTTCCTCAAATTGATTGGCGGTCCGTTCCTCAAATTGATTGGCGG<br>TC<br>(SEQ ID NO: 42) | | 48 | *F. oxysporum* |
| Fox2R | D | GTTGGGACTCGCGTTAATTCGGTTGGGACTCGCGTTAATTCG<br>(SEQ ID NO: 43) | | 42 | *F. oxysporum* |
| Fox2-A | DA | CGTTCCTCAAATTGATTGGCGGTCAAAAAAAAAACGTTCCTCAAAT<br>TGATTGGCGGTC<br>(SEQ ID NO: 44) | | 58 | *F. oxysporum* |
| Fo1R-A | DA | GTTGGGACTCGCGTTAATTCGAAAAAAAAAAGTTGGGACTCGCGTT<br>AATTCG<br>(SEQ ID NO: 45) | | 52 | *F. oxysporum* |
| Positive control Probe | | | | | |
| ITS2 | M | GCTGCGTTCTTCATCGATGC<br>(SEQ ID NO: 46) | White et al. 1990 | 20 | Fungi |
| ITS4 | M | TCCTCCGCTTATTGATATGC<br>(SEQ ID NO: 47) | White et al. 1990 | 20 | Fungi & oomycete |
| ITS2R | D | GCTGCGTTCTTCATCGATGCGCTGCGTTCTTCATCGATGC<br>(SEQ ID NO: 48) | | 40 | Fungi |
| ITS4R | D | TCCTCCGCTTATTGATATGCTCCTCCGCTTATTGATATGC<br>(SEQ ID NO: 49) | | 40 | Fungi & oomycete |
| ITS2R-A | DA | GCTGCGTTCTTCATCGATGCAAAAAAAAAAGCTGCGTTCTTCATCG<br>ATGC<br>(SEQ ID NO: 50) | | 50 | Fungi |
| ITS4R-A | DA | TCCTCCGCTTATTGATATGCAAAAAAAAAATCCTCCGCTTATTGAT<br>ATGC<br>(SEQ ID NO: 51) | | 50 | Fungi & oomycete |
| ITS2-A10 | M-A10 | GCTGCGTTCTTCATCGATGCAAAAAAAAAA<br>(SEQ ID NO: 52) | | 30 | Fungi |
| ITS4-A10 | M-A10 | TCCTCCGCTTATTGATATGCAAAAAAAAAA<br>(SEQ ID NO: 53) | | 30 | Fungi & oomycete |
| ITS2-A20 | M-A20 | GCTGCGTTCTTCATCGATGCAAAAAAAAAAAAAAAAAAAA<br>(SEQ ID NO: 54) | | 40 | Fungi |
| ITS4-A20 | M-A20 | TCCTCCGCTTATTGATATGCAAAAAAAAAAAAAAAAAAAA<br>(SEQ ID NO: 55) | | 40 | Fungi & oomycete |
| Internal control Probe | | | | | |
| ITS2-2-1 | M | GCTGCGTTGATCATCGATGC<br>(SEQ ID NO: 56) | Zhang et al. 2008 | 20 | None |
| ITS2-2-1R | D | GCTGCGTTGATCATCGATGCGCTGCGTTGATCATCGATGC<br>(SEQ ID NO: 57) | | 40 | None |
| ITS2-2-1R-A | DA | GCTGCGTTGATCATCGATGCAAAAAAAAAAGCTGCGTTGATCATCG<br>ATGC<br>(SEQ ID NO: 58) | | 50 | None |

TABLE 2-continued

Probe name, type, sequence, length and targeted species used in this study.

| Probe name | Probe type[a] | Probe sequence | Reference[b] | Probe Length | Probe target |
|---|---|---|---|---|---|
| ITS2-2-1-A10 | M-A10 | GCTGCGTTGATCATCGATGCAAAAAAAAAA (SEQ ID NO: 59) | | 30 | None |
| ITS2-2-1-A20 | M-A20 | GCTGCGTTGATCATCGATGCAAAAAAAAAAAAAAAAAAAA (SEQ ID NO: 60) | | 40 | None |

[a]D = dimer, DA = dimer with 10 adenine nucleotides(poly-A) spacer, M = monomer, M-A10 = monomer with 10 adenine nucleotides (poly-A10) tail and M-A20 = monomer with 20 adenine nucleotides(poly-A20) tail.
[b]Reference for literature citations. Oligonucleotide probes that do not have a reference were modifications from referenced probes by the authors for this study.

Hybridization

Hybridization was carried out as described previously (Zhang et al., 2007, 2008). The test ITS amplicons from either target or non-target materials were labeled and hybridized using the Gene Images AlkPhos Direct Labeling (GE Healthcare Bio-Sciences Corp., Piscataway, N.J., USA) and Detection System with CDP-Star (Topix Inc., Bedford, Mass., USA). Before use, the arrays were pre-hybridized at 55° C. for 15 min and hybridized with 100 ng (10 μl of 10 m/μl) of labeled ITS amplicon at 55° C. for 2 h. After two primary washes and two secondary washes, the detection reagent was added to the array to react for an hour, followed by 30 min of film exposure. Chemiluminescence was detected using Kodak Biomax Light film. Developed films were scanned by an Aficio MP C6000 Color Copier/Scanner (Ricoh Americas Corporation, West Caldwell, N.J., USA) and read with ImageJ 1.33u (National Institutes of Health, MD, USA).

Array Sensitivity

The signal intensity for hybridization was measured as the average inverted gray value for the quadruplicate spots for each detector oligonucleotide on the array after the background gray values were subtracted. Since in 8-bit grayscale images, the darkest picture corresponds to the lowest value, each value was inverted by subtracting its reading from 255 (i.e. inverted gray value=255-gray value readings). Each experiment was conducted at least twice. The signal intensity of the monomers was compared vis-à-vis those of the dimer, DA and where applicable, M-A10 and M-A20 for each isolate.

Two isolates, R. solani (#98) and P. aphanidermatum (#99), were used to determine the detection limit of the PCR-coupled macroarray method. The genomic DNA of #98 and #99 was 10× serially diluted from 1 ng/μl to $1\times10^{-10}$ ng/μl prior to a standard ITS PCR. Following ITS amplification, hybridization was conducted as described above. Ten μl of purified ITS PCR product was used for hybridization and gel electrophoresis. The experiments were conducted twice. To determine whether DNA from the host and other co-inhabiting fungi would interfere with the target species detection, the target DNA was 10× serially diluted (from 1 ng/μl to $1\times10^{-4}$ ng/μl) and mixed with 1 ng of plant DNA. Two ul of the mixture were used for PCR amplification in a 25 μl reaction mix (Table 3). Plant DNA was derived from clean greenhouse grown Poa annua with no history of disease infection. Serially diluted genomic DNA of the target species (from 1 ng/μl to $1\times10^{-2}$ ng/μl of #98 or #99) was mixed in same ratio with the serially diluted genomic DNA from three common turfgrass-associated fungi, C. trifolii, T. virens, and M. elongata (Table 3). PCR amplification and hybridization were done as explained above. Control experiments were done to test if the observed results were due to skewed amplification by PCR, by mixing 2.5 ng of purified PCR products of each of the test sample (P. annua, C. trifolii, T. virens, M. elongata, and the target species) to final volume of 10 μl before macroarray hybridization.

TABLE 3

Amount of target species DNA, common co-inhabiting non-target fungal species DNA, and host DNA used in 25 μl-PCR reactions for assessment of hybridization interference

| Reaction number | Target DNA amount (ng)[a] | C. trifolii DNA amount (ng) | M. elongata DNA amount (ng) | T. virens DNA amount (ng) | Host DNA amount (ng) | Hybridization signal observed[b] |
|---|---|---|---|---|---|---|
| 1 | $10^{-4}$ | 0 | 0 | 0 | 1 | yes |
| 2 | $10^{-3}$ | 0 | 0 | 0 | 1 | yes |
| 3 | $10^{-2}$ | 0 | 0 | 0 | 1 | yes |
| 4 | $10^{-1}$ | 0 | 0 | 0 | 1 | yes |
| 5 | $10^{-2}$ | $10^{-2}$ | $10^{-2}$ | $10^{-2}$ | 1 | yes |
| 6 | $10^{-1}$ | $10^{-1}$ | $10^{-1}$ | $10^{-1}$ | 1 | yes |
| 7 | 1 | 1 | 1 | 1 | 1 | yes |

[a] Target species used were Rhizoctonia solani isolate #98 or Pythium aphanidermatum isolate #99. The non-target fungal species used were Curvularia trifolii, Trichoderma virens, and Mortierella elongata while the host species was Poa annua.
[b] Yes implies that a hybridization signal was observed.

Array Validation

The macroarray was validated with DNA extracted from plant tissues or soils infested by the target species. DNA was extracted using UltraClean Soil DNA kit (MoBio Laboratories, Inc., Solana Beach, Calif., USA) or DNeasy Plant Mini kit (Qiagen Inc., Valencia, Calif., USA) depending on the material. Microscopic observation was also performed to check for presence of fungal or oomycete structures in the substrate.

Array Specificity

To assess the specificity of detection by the array, fungal and oomycete strains that differ from the target species by 1 to 3 bases of the probe sequence were tested for cross-reaction against the array (Table 4). DNA extraction, purification and hybridization were done as described above. Other fungal and oomycete species often found associated with turfgrasses were also included in the experiments to test the array's ability to discriminate non-target species.

TABLE 4

DNA sequence mismatches between target and closely related non-target species at the ITS region where the probe was designed.

| Target Species[b] | Probe | Probe sequence | Non-target[a] Species with 1 nt mismatch | Mismatch position |
|---|---|---|---|---|
| Pa | Pa1 | GGAGAGAGATGGCAGAATGTGAG (SEQ ID NO: 1) | *P. torulosum* (#122) | GGAGAGA<u>A</u>ATGGCAGAATGTGAG (SEQ ID NO: 61) |
| | Pa2 | GGGAGAGAGATGGCAGAATGTGAG (SEQ ID NO: 2) | — | NA |
| | Pa3 | GAGGTGTACCTGAATTGTGTGAGG (SEQ ID NO: 3) | — | NA |
| Rs | Rs2 | CAGTGTTATGCTTGGTTCCACTC (SEQ ID NO: 16) | — | NA |
| | Rs3 | TGTTGAAACTTAGTATTAGATGCGT (SEQ ID NO: 17) | — | NA |
| | Rs4 | GAGTGGAACCAAGCATAACACTG (SEQ ID NO: 18) | — | NA |
| Fs | Fs4 | TCGCGTAGTAGCTAACACCTCGC (SEQ ID NO: 25) | — | NA |
| | Fs6 | CCTGTGAACATACCTAAACGTTG (SEQ ID NO: 26) | *F. solani* (#F19) | CCTGTGAACATACCT<u>A</u>AAACGTTG (SEQ ID NO: 67) |
| | Fs13 | TTATACAACTCATCAACCCTGTGA (SEQ ID NO: 27) | *F. solani* (#F3) | TTA<u>T</u>TCAACTCATCAACCCTGTGA (SEQ ID NO: 69) |
| Fo | Fo1 | CGTTCCTCAAATTGATTGGCGGTC (SEQ ID NO: 40) | — | NA |
| | Fox2 | GTTGGGACTCGCGTTAATTCG (SEQ ID NO: 41) | — | NA |

| Target Species[b] | Species with 2 nt mismatch | Mismatch position | Species with 3 nt mismatch | Mismatch positions |
|---|---|---|---|---|
| Pa | *P. volutum* (#124p-1) | GGAGAGA<u>AA</u>TGGCAGATGTGAG (SEQ ID NO: 62) | — | NA |
| | *P. torulosum* (#122) | <u>A</u>GGAGAGA<u>A</u>ATGGCAGAATGTGAG (SEQ ID NO: 63) | *P. volutum* (#124p-1) | <u>A</u>GGAGAGA<u>A</u>ATGGCAGATGTGAG (SEQ ID NO: 64) |
| | *P. volutum* (#124p-1), *P. torulosum* (#122) | GAGGTGTACCTGTCTTGTGTGAGG (SEQ ID NO: 65) | — | NA |
| Rs | — | NA | — | NA |
| | — | NA | — | NA |
| | — | NA | — | NA |
| Fs | *F. equiseti* (#S2) | T<u>A</u>GCGTGAGTAGCTAACACCTCG<u>T</u> (SEQ ID NO: 66) | — | NA |
| | *F. equiseti* (#S2) | CCTGTGAACATACCTACGTTG (SEQ ID NO: 68) | — | NA |
| | *F. oxysporum* (#F2, #S4), *F. equiseti* (#S2) | TTATACAACTCATCAA<u>AC</u>CCCTGTGA (SEQ ID NO: 70) | — | NA |

TABLE 4-continued

DNA sequence mismatches between target and closely related non-target species at the ITS region where the probe was designed.

| Fo | *F. equiseti* (#S2) | CGTCCCTCAAATCGATTGGGGGTC (SEQ ID NO: 71) | — | NA |
| --- | --- | --- | --- | --- |
| — | NA | | *F. equiseti* (#S2) | GTTGGGACTCGCGGTAACCCG (SEQ ID NO: 72) |

[a]indicates no candidate species was available with the specified mismatch, NA = not applicable, sequences that caused cross-hybridization are in boldface.
[b]Pa = *Phythium aphanidermatum*, Rs = *Rhizoctonia solani*, Fs = *Fusarium solani*, Fo = *Fusarium oxysporum*

TABLE 5

Two-way ANOVA for hybridization results of monomers printed on a membrane with and without other probe types, tested against four isolates (N = 24).

ANOVA

| Source of Variation | SS | df | MS | F | P-value |
| --- | --- | --- | --- | --- | --- |
| Monomer type | 192.13 | 1 | 192.13 | 0.21 | 0.65 |
| Isolate | 5154.76 | 3 | 1718.25 | 1.92 | 0.17 |
| Interaction (Monomer type x Isolate) | 257.45 | 3 | 85.82 | 0.09 | 0.96 |
| Error | 14349.09 | 16 | 896.82 | | |
| Total | 19953.44 | 23 | | | |

TABLE 6

Comparison of hybridization results between target and non-target species based on monomer, dimer, and dimer with poly-A spacer probes.

| Test species[a] | ID #[b] | \multicolumn{9}{c}{*Pythium aphanidermatum*} | \multicolumn{8}{c}{*Rhizoctonia solani*} |
| --- | --- | --- | --- | --- | --- | --- | --- | --- | --- | --- | --- | --- | --- | --- | --- | --- | --- | --- |
| | | M Pa1 | M Pa2 | M Pa3 | D Pa1R | D Pa2R | D Pa3R | DA Pa1R-A | DA Pa2R-A | DA Pa3R-A | M Rs2 | M Rs3 | M Rs4 | D Rs2R | D Rs3R | D Rs4R | DA Rs2R-A | DA Rs3R-A |
| Ct | #185 | −[d] | − | − | − | − | − | − | − | − | − | − | − | − | − | − | − | − |
| Fe | #S2 | − | − | − | − | − | − | − | − | − | − | − | − | − | − | − | − | − |
| Fo | #F2 | − | − | − | − | − | − | − | − | − | − | − | − | − | − | − | − | − |
| Fo | #S4 | − | − | − | − | − | − | − | − | − | − | − | − | − | − | − | − | − |
| Fs | #F3 | − | − | − | − | − | − | − | − | − | − | − | − | − | − | − | − | − |
| Fs | #F19 | − | − | − | − | − | − | − | − | − | − | − | − | − | − | − | − | − |
| Me | #141 | − | − | − | − | − | − | − | − | − | − | − | − | − | − | − | − | − |
| Poa | NA | − | − | − | − | − | − | − | − | − | − | − | − | − | − | − | − | − |
| Pa | #60 | ⊗ | + | + | + | + | + | + | + | + | − | − | − | − | − | − | − | − |
| Pa | #99 | ⊗ | + | + | + | + | + | + | + | + | − | − | − | − | − | − | − | − |
| Pr | #123p | − | − | − | − | − | − | − | − | − | − | − | − | − | − | − | − | − |
| Pt | #122 | − | − | − | − | − | − | − | − | − | − | − | − | − | − | − | − | − |
| Pv | #124p-1 | − | − | − | − | − | − | − | − | − | − | − | − | − | − | − | − | − |
| Wc | #10 | − | − | − | − | − | − | − | − | − | − | − | − | − | − | − | − | − |
| Wc | #158 | − | − | − | − | − | − | − | − | − | − | − | − | − | − | − | − | − |
| Rs | #RH 20 | − | − | − | − | − | − | − | − | − | + | + | + | + | + | + | + | + |
| Rs | #98 | − | − | − | − | − | − | − | − | − | + | + | + | + | + | + | + | + |
| Tv | #126-L | − | − | − | − | − | − | − | − | − | − | − | − | − | − | − | − | − |

| Test species[a] | Rhizoctonia solani DA Rs4R-A | \multicolumn{9}{c}{*Fusarium solani*} | \multicolumn{6}{c}{*Fusarium oxysporum*} |
| --- | --- | --- | --- | --- | --- | --- | --- | --- | --- | --- | --- | --- | --- | --- | --- | --- |
| | | M Fs4 | M Fs6 | M Fs13 | D Fs4R | D Fs6R | D Fs13R | DA Fs4R-A | DA Fs6R-A | DA Fs13R-A | M Fo1 | M Fox2 | D Fo1R | D Fox2R | DA Fo1R-A | DA Fox2R-A |
| Ct | − | − | − | − | − | − | − | − | − | − | − | − | − | − | − | − |
| Fe | − | − | − | − | − | − | − | − | − | − | − | − | ⊕ | − | ⊕ | − |
| Fo | − | − | − | − | − | − | − | − | − | − | + | + | + | + | + | + |
| Fo | − | − | − | − | − | − | − | − | − | − | + | − | + | + | + | + |
| Fs | − | + | + | − | + | + | ⊕ | + | + | ⊕ | − | − | − | − | − | − |
| Fs | − | + | − | + | + | ⊕ | + | + | ⊕ | + | − | − | − | − | − | − |
| Me | − | − | − | − | − | − | − | − | − | − | − | − | − | − | − | − |
| Poa | − | − | − | − | − | − | − | − | − | − | − | − | − | − | − | − |
| Pa | − | − | − | − | − | − | − | − | − | − | − | − | − | − | − | − |

TABLE 6-continued

Comparison of hybridization results between target and non-target species based on monomer, dimer, and dimer with poly-A spacer probes.

| | | | | | | | | | | | | | | | | |
|---|---|---|---|---|---|---|---|---|---|---|---|---|---|---|---|---|
| Pa | − | − | − | − | − | − | − | − | − | − | − | − | − | − | − | − |
| Pr | − | − | − | − | − | − | − | − | − | − | − | − | − | − | − | − |
| Pt | − | − | − | − | − | − | − | − | − | − | − | − | − | − | − | − |
| Pv | − | − | − | − | − | − | − | − | − | − | − | − | − | − | − | − |
| Wc | − | − | − | − | − | − | − | − | − | − | − | − | − | − | − | − |
| Wc | − | − | − | − | − | − | − | − | − | − | − | − | − | − | − | − |
| Rs | + | − | − | − | − | − | − | − | − | − | − | − | − | − | − | − |
| Rs | + | − | − | − | − | − | − | − | − | − | − | − | − | − | − | − |
| Tv | − | − | − | − | − | − | − | − | − | − | − | − | − | − | − | − |

[a] Ct = Curvularia trifolii, Fe = Fusarium equiseti, Fo = Fusarium oxysporum, Fs = Fusarium solani, Me = Mortierella elongata, Poa = Poa annua, Pa = Pythium aphanidermatum, Pr = Pythium rostrum, Pt = Pythium torulosum, Pa = Pythium volutum, Wc = Waitea circinata var. circinata, Rs = Rhizoctonia solani, Tv = Trichoderma virens.
[b] Collection ID/accession number.
[c] A list of 33 probe names derived from 4 target species and 3 probe types, where M = monomer, D = dimer, and DA = dimer with 10 adenine (poly-A) spacer.
[d] − indicates no hybridization signal was observed, + indicates a hybridization signal was observed. All isolates were tested on three probes for each target in quadruplicate. False negatives (⊗) were observed in M probe Pa1 for *P. aphanidermatum* test isolates (#60 and #99). False positives (⊕) between *F. oxysporum* probes (D and DA) and *F. equiseti*, and between *F. solani* probes (D and DA) and non-target *F. solani* strains.

Statistical Analysis

Every probe was spotted four times on the macroarray and measured individually, and the hybridization experiment was repeated at least once. Quantitative data were analyzed using a two-way ANOVA (isolate and probe type) with SAS (version 9.2) statistical software. A P value <0.05 was considered significant. Specifically, signal intensities of hybridization of monomers printed on a membrane with and without other probe types were analyzed using a 2×4 factorial design.

EXAMPLE 2

Additional Dimeric Oligonucleotide Probes

Additional dimeric probes that hybridize to target sequences that are specific to over 50 turf grass pathogens were designed as described in Example 1. The sequences for these probes, as well as the pathogenic target, are shown in Table 7. Positive and negative control probes are also included in this table. These probes may be evaluated and employed in macroarray analyses, as described above in Example 1.

TABLE 7

Additional dimeric oligonucleotide probes

| Pathogen (Probe Target) | Probe Name | Probe Sequence | Probe Length |
|---|---|---|---|
| *Brumeria graminis* | Bg_2D | TGTAACTCTCCGCGTAGTAATATGTAACTCTCCGCGTAGTAATA (SEQ ID NO: 73) | 44 |
| | Bg_3D | GTTGACCCTCCACCCGTGTCGATTAGTTGACCCTCCACCCGTGTCGATTA (SEQ ID NO: 74) | 50 |
| | Bg_4D | AGCGTCCGTAACAACCTCTCAAGCCTAGCGTCCGTAACAACCTCTCAAGCCT (SEQ ID NO: 75) | 52 |
| | Bg_5D | GAGCGTCCGTAACAACCTCTCAAGCCTGAGCGTCCGTAACAACCTCTCAAGCCT (SEQ ID NO: 76) | 54 |
| *Bipolaris zeicola* | Bz-4D[a] | TTTCGGAGCGCAGCACATATTTTGTTTCGGAGCGCAGCACATATTTTG (SEQ ID NO: 77) | 48 |
| | Bz-5D[a] | CTGGGAGACTCGCCTTAAAACGATTGCTGGGAGACTCGCCTTAAAACGATTG (SEQ ID NO: 78) | 52 |
| | Bz-6D | GCTTGGTGTTGGGCGTTTTTTGTCTCCGCTTGGTGTTGGGCGTTTTTTGTCTCC (SEQ ID NO: 79) | 54 |
| | Bz-7D | CATTTTTAACTTTTGACCTCGGATCATTTTTAACTTTTGACCTCGGAT (SEQ ID NO: 80) | 48 |
| *Colletotrichum cereale* | Cc_2D | CTACCAGGGGACGTGGCGCCCGCCGCTACCAGGGGACGTGGCGCCCGCCG (SEQ ID NO: 81) | 50 |
| | Cc_3D | CCAGGGGACGTGGCGCCCGCCGGACCAGGGGACGTGGCGCCCGCCGGA (SEQ ID NO: 82) | 48 |
| | Cc_7D | ACGACGTTTCTTCTGAGTGGCACAACGACGTTTCTTCTGAGTGGCACA (SEQ ID NO: 83) | 48 |
| | Cc_9D | CTGAGTGGCACAAGCAAATAATTCTGAGTGGCACAAGCAAATAATT (SEQ ID NO: 84) | 46 |
| *Eudarluca caricis* | Ec_2D | CAGAAACCGCTCTATACTCGGCAGAAACCGCTCTATACTCGG (SEQ ID NO: 85) | 42 |
| | Ec_3D | GCCTGATTCTCCCCATGTCTTGCCTGATTCTCCCCATGTCTT (SEQ ID NO: 86) | 42 |
| | Ec_6D | ACGATAGCCTGAAGCGCAGCACATACGATAGCCTGAAGCGCAGCACAT (SEQ ID NO: 87) | 48 |
| | Ec_7D | CAGCGTCAGTAACAAGTAATTCAGCGTCAGTAACAAGTAATT (SEQ ID NO: 88) | 42 |

TABLE 7-continued

Additional dimeric oligonucleotide probes

| Pathogen (Probe Target) | Probe Name | Probe Sequence | Probe Length |
|---|---|---|---|
| Puccinia coronata | Pc_3D | AGAATAGAGTGCACTTGATTGTGGCTAGAATAGAGTGCACTTGATTGTGGCT (SEQ ID NO: 89) | 52 |
| | Pc_6D | TTATTAGGAGAGTTACATTACCCTTATTAGGAGAGTTACATTACCC (SEQ ID NO: 90) | 46 |
| | Pc_7D | CTTGGTTGCATGATTTGAAAGAGTCACTTGGTTGCATGATTTGAAAGAGTCA (SEQ ID NO: 91) | 48 |
| | Pc_9D | TTAAAAAGACTTGGTTGCATTTAAAAAGACTTGGTTGCAT (SEQ ID NO: 92) | 40 |
| Puccinia persistens var triticina | Pp_t_1D | GCATTCTTTATTGAATGTTCACAGCATTCTTTATTGAATGTTCACA (SEQ ID NO: 93) | 48 |
| | Pp_t_2D | CACTTCTTTGCATGATTTGAAAGACACTTCTTTGCATGATTTGAAAGA (SEQ ID NO: 94) | 48 |
| | Pp_t_4D | AATCTTACCCAAACTTTTAACACAATCTTACCCAAACTTTTAACAC (SEQ ID NO: 95) | 46 |
| | Pp_t_7D | GTTTAGTGGATGTTGAGTGTTGCTGTCGTTTAGTGGATGTTGAGTGTTGCTGTC (SEQ ID NO: 96) | 54 |
| Puccinia striiformis | Ps_2D | ACGTAACTTCTTTATTGAATGTTGCACGTAACTTCTTTATTGAATGTTGC (SEQ ID NO: 97) | 50 |
| | Ps_7D | GTCACTTTTCTATAAGTTGGATGTCACTTTTCTATAAGTTGGAT (SEQ ID NO: 98) | 44 |
| | Ps_9D | CATCTTATTTAAGGGAGACTCCATCTTATTTAAGGGAGACTC (SEQ ID NO: 99) | 44 |
| | Ps_10D | GAGACTCCTAAAAACCCAATGAGACTCCTAAAAACCCAAT (SEQ ID NO: 100) | 40 |
| Puccinia graminis | Pg_1D | ACTTTTAAAAACTTGGTTGCATGAACTTTTAAAAACTTGGTTTGCATGA (SEQ ID NO: 101) | 48 |
| | Pg_5D | TTAGTGGATGTTGAGTGTTGCTGTACCTTAGTGGATGTTGAGTGTTGCTGTACC (SEQ ID NO: 102) | 54 |
| | Pg_7D | CACTTGCCATCTTGTTTGTTACACTTGCCATCTTGTTTGTTA (SEQ ID NO: 103) | 42 |
| | Pg_8D | GAGTATACGTAACATTCTTAATTGAGAGTATACGTAACATTCTTAATTGA (SEQ ID NO: 104) | 50 |
| Puccinia graminis f. sp. Tritici | Pg_T1d | GCCATCTTTTTTGTAACAAGAGACGCCATCTTTTTTGTAACAAGAGAC (SEQ ID NO: 105) | 48 |
| | Pg_T2d | CCCAATATCTATTTTTTTAAGACCTCCCAATATCTATTTTTTTAAGACCT (SEQ ID NO: 106) | 52 |
| | Pg_T4d | AACAAGAGACTCCTAAAACCCAAACAAGAGACTCCTAAAACCCA (SEQ ID NO: 107) | 44 |
| | Pg_T3d | TGGGTTTTAGGAGTCTCTTGTTTGGGTTTTAGGAGTCTCTTGTT (SEQ ID NO: 108) | 44 |
| Pythium volutum | Pv_2D | GTTCTGTGCCTTCTCTTGGGAGGTTCTGTGCCTTCTCTTGGGAG (SEQ ID NO: 109) | 44 |
| | Pv_3D | GAAGGTTGGCTGCAAATGTAGTGAAGGTTGGCTGCAAATGTAGT (SEQ ID NO: 110) | 48 |
| | Pv_4D | CTGTATGCGCGGTCTTCCGATGTACTGTATGCGCGGTCTTCCGATGTA (SEQ ID NO: 111) | 48 |
| | Pv_10D | CTTGTGTTTGAGAGAAGTGCTGACCCTTGTGTTTGAGAGAAGTGCTGACC (SEQ ID NO: 112) | 50 |
| Pythium torulosum/ | Pt_1D | GCGGTTTTGCCGATGTACTTTTAAACGCGGTTTTGCCGATGTACTTTTAAAC (SEQ ID NO: 113) | 52 |
| | Pt_2D | GTACCTGTCTTGTGTGAGGCAACGGTACCTGTCTTGTGTGAGGCAACG (SEQ ID NO: 114) | 48 |
| | Pt_3D | TGTCTTGTGTGAGGCAACGGTCTGTGTCTTGTGTGAGGCAACGGTCTG (SEQ ID NO: 115) | 48 |
| | Pt_4D | GTACCTGTCTTGTGTGAGGCAACGGGTACCTGTCTTGTGTGAGGCAACGG (SEQ ID NO: 116) | 50 |
| Pythium arrhenomanes | Parr_1D | TGTAATTTGTTTTGTGCCTTCTTTCTGTAATTTGTTTTGTGCCTTCTTTC (SEQ ID NO: 117) | 52 |
| | Parr_2D | GAAAGAAGGCACAAAACAAAATTACAGAAAGAAGGCACAAAACAAAATTACA (SEQ ID NO: 118) | 52 |

TABLE 7-continued

Additional dimeric oligonucleotide probes

| Pathogen (Probe Target) | Probe Name | Probe Sequence | Probe Length |
|---|---|---|---|
| *Pythium deliense* | Pd_1D | TACCTGATTTGTGTGAGGCAATGGTTACCTGATTTGTGTGAGGCAATGGT (SEQ ID NO: 119) | 50 |
| | Pd_2D | TCATGTTCTGTGCTCTCTCTCGGGATCATGTTCTGTGCTCTCTCTCGGGA (SEQ ID NO: 120) | 50 |
| | Pd_3D | CGTTGACTCCCTTTTCGGAGGAGAACGTTGACTCCCTTTTCGGAGGAGAA (SEQ ID NO: 121) | 50 |
| | Pd_4D | GCTTAATTGTGGTCTGCCGATGTATTTGCTTAATTGTGGTCTGCCGATGTATTT (SEQ ID NO: 122) | 54 |
| *Pythium rostratifingens* | Pr_2D | GAGTCGGCTAAACGAAGGTCGGGGAGTCGGCTAAACGAAGGTCGGG (SEQ ID NO: 123) | 46 |
| | Pr_5D | GACTCCGGTTTTTCTATTGCGTTGCTGACTCCGGTTTTTCTATTGCGTTGCT (SEQ ID NO: 124) | 52 |
| | Pr_6D | TTGGAGAAGGAGCAGAGGTGAAGTTGGAGAAGGAGCAGAGGTGAAG (SEQ ID NO: 125) | 44 |
| | Pr_10D | CTCCAGAGCACGCTACCGAGGTCTCCAGAGCACGCTACCGAGGT (SEQ ID NO: 126) | 44 |
| *Pythium rostratum* | Prm_1D | GGACTGATGTGCGCTTGTCGCATGTGGACTGATGTGCGCTTGTCGCATGT (SEQ ID NO: 127) | 50 |
| | Prm_6D | TTAAACCATACCATAAGTACTGATTTTAAACCATACCATAAGTACTGATT (SEQ ID NO: 128) | 50 |
| | Prm_9D | TCTCCGCTGAGAGTTTGTGTGTGTCTCCGCTGAGAGTTTGTGTGTG (SEQ ID NO: 129) | 54 |
| | Prm_10D | CTCTCCGCTGAGAGTTTGTGTGTGCTCTCCGCTGAGAGTTTGTGTGTG (SEQ ID NO: 130) | 42 |
| *Pyrhium aphanidermatum* | Pa_1D | GCTGCTCTTGGACGCCCTGTTTTCGCTGCTCTTGGACGCCCTGTTTTC (SEQ ID NO: 131) | 52 |
| | Pa_2D | GCTGCTCTTGGACGCCCTGTTGCTGCTCTTGGACGCCCTGTT (SEQ ID NO: 132) | 42 |
| | Pa_4D | GACTGTTTGCAATTTATTGTGAGACTGTTTGCAATTTATTGTGA (SEQ ID NO: 133) | 44 |
| | Pa_5D | GAAAGTTTATGGTTTTAATCTAGAAAGTTTATGGTTTTAATCTA (SEQ ID NO: 134) | 44 |
| *Pythium myriotylum* | Pm_1D | GATTAGAGATGGCAGAATGTGAGGTGGATTAGAGATGGCAGAATGTGAGGTG (SEQ ID NO: 135) | 52 |
| | Pm_2D | GCTCTGCGCGAGTGGGCGACTTCGGTGCTCTGCGCGAGTGGGCGACTTCGGT (SEQ ID NO: 136) | 52 |
| | Pm_4D | CCTGTCTTGTGTGGGGCAATGGTCTGCCTGTCTTGTGTGGGGCAATGGTCTG (SEQ ID NO: 137) | 52 |
| | Pm_5D | CCTGTCTTGTGTGGGGCAATGGTCCTGTCTTGTGTGGGGCAATGGT (SEQ ID NO: 138) | 46 |
| *Pythium arrhenomanes* | Par_3D | GGTTGTCCGCAAGTGTAGTTAATTCGGTTGTCCGCAAGTGTAGTTAATTC (SEQ ID NO: 139) | 50 |
| | Par_5D | AGATGGCAGATGTGAGGTGTCTAGATGGCAGATGTGAGGTGTCT (SEQ ID NO: 140) | 44 |
| | Par_6D | GTGTCTGAGAGAAGTGTGACCTGTGTCTGAGAGAAGTGTGACCT (SEQ ID NO: 141) | 44 |
| | Par_7D | AGTGGTTATTGCTCTTGGACGCAGTGGTTATTGCTCTTGGACGC (SEQ ID NO: 142) | 44 |
| *Rhizotonia solani* | Rs_2D | AACGAATGTAATTGATGTAACGAACGAATGTAATTGATGTAACG (SEQ ID NO: 143) | 44 |
| | Rs_4D | CTGGATCTCAGTGTTATGCTTGGCTGGATCTCAGTGTTATGCTTGG (SEQ ID NO: 144) | 46 |
| | Rs_5D | ACCGCTTCTAATAGTCCATTGACACCGCTTCTAATAGTCCATTGAC (SEQ ID NO: 145) | 46 |
| | Rs_9D | GTAACGCATCTAATACTAAGTTTGTAACGCATCTAATACTAAGTTT (SEQ ID NO: 146) | 46 |
| *Ceratobasidium cereale* | Cr_4D | CCGTCCAATACATAAAATCTTACCGTCCAATACATAAAATCTTA (SEQ ID NO: 147) | 44 |
| | Cr_6D | TAATCAGAATGTAATCGATGTAAACGTAATCAGAATGTAATCGATGTAAACG (SEQ ID NO: 148) | 52 |
| | Cr_7D | GTAAACGCATCTATAAACTAAGGTAAACGCATCTATAAACTAAG (SEQ ID NO: 149) | 44 |
| | Cr_8D | GGCTTTTGTTTTGGATTTGGAGGTGGCTTTTGTTTTGGATTTGGAGGT (SEQ ID NO: 150) | 48 |

TABLE 7-continued

Additional dimeric oligonucleotide probes

| Pathogen (Probe Target) | Probe Name | Probe Sequence | Probe Length |
|---|---|---|---|
| *Waitea circinata* | Wc_1D | GTCCCTGTAGACTCTGCTTCAGTCCCTGTAGACTCTGCTTCA (SEQ ID NO: 151) | 42 |
|  | Wc_2D | CTAGTGTTTCTAGTATGTGCACTAGTGTTTCTAGTATGTGCA (SEQ ID NO: 152) | 42 |
|  | Wc_3D | GTAATAGATCTATGTGGATACGGTAATAGATCTATGTGGATACG (SEQ ID NO: 153) | 44 |
|  | Wc_3D | TGAAGCAGAGTCTACAGGGACTGAAGCAGAGTCTACAGGGAC (SEQ ID NO: 154) | 42 |
| *Rhizoctonia zeae* | Wcz_1D | CTTCTGTAATAGATCTATGTGGATACGCTTCTGTAATAGATCTATGTGGATACG (SEQ ID NO: 155) | 54 |
|  | Wcz_2D | CATGAATCTCTCAAATACAATGATTTCATGAATCTCTCAAATACAATGATTT (SEQ ID NO: 156) | 52 |
|  | Wcz_3D | CATGAATCTCTCAAATACAATGACATGAATCTCTCAAATACAATGA (SEQ ID NO: 157) | 46 |
|  | Wcz_4D | CCTTCTGTAATAGATCTATGTGCCTTCTGTAATAGATCTATGTG (SEQ ID NO: 158) | 44 |
| *Waitea circinata* var. *circinata* | Wcc_4D | TTATACACACACAATAGTCATTGTTATACACACACAATAGTCATTG (SEQ ID NO: 159) | 46 |
|  | Wcc_8D | CCTGTGCACCTTTTGTAGTATTACCCTGTGCACCTTTTGTAGTATTAC (SEQ ID NO: 160) | 48 |
|  | Wcc_11D | CAAATGTATTAGCTGGGGTTTATATAGCAAATGTATTAGCTGGGGTTTATATAG (SEQ ID NO: 161) | 54 |
|  | Wcc_12D | TGGAAGCTGTTGGCGCAAGTCGATGGAAGCTGTTGGCGCAAGTCGA (SEQ ID NO: 162) | 50 |
| *Rhizotonia oryzae* | Wco_1D | TATTTTGAATCATTATTATTTGGACTATTTTGAATCATTATTATTTGGAC (SEQ ID NO: 163) | 50 |
|  | Wco_2D | CTTGGAAGTTTGTCGGCGCAAGTCTTGGAAGTTTGTCGGCGCAAGT (SEQ ID NO: 164) | 46 |
|  | Wco_3D | TGAGTGTCATGAATCTCTCAAATATGAGTGTCATGAATCTCTCAAATA (SEQ ID NO: 165) | 48 |
|  | Wco_4D | ATTTGGACTTGGAAGTTTGTCGGCATTTGGACTTGGAAGTTTGTCGGC (SEQ ID NO: 166) | 48 |
|  | Wco_6D | TTGGAAGTTTGTCGGCGCAAGTTTGGAAGTTTGTCGGCGCAAGT (SEQ ID NO: 167) | 46 |
| *Sclerotinia homoeocarpa* | Sh_1D | TCCAACCCTTGTGTATCTCTACCATCCAACCCTTGTGTATCTCTACCA (SEQ ID NO: 168) | 48 |
|  | Sh_2D | CCTTGTGTATCTCTACCATGTTCCTTGTGTATCTCTACCATGTT (SEQ ID NO: 169) | 44 |
|  | Sh_4D | ACAGCCTCAGCGCCCTCCGGGGCCACAGCCTCAGCGCCCTCCGGGGCC (SEQ ID NO: 170) | 48 |
|  | Sh_5D | AGGAAAATCACAACTCTGAATTGAGGAAAATCACAACTCTGAATTG (SEQ ID NO: 171) | 46 |
| *Typhula incarnata* | Ta_2D | ATGGGGTTCTGCTTCTAATCGTCATGGGGTTCTGCTTCTAATCGTC (SEQ ID NO: 172) | 46 |
|  | Ta_3D | CTCTTTGTGGTGCCAGACTATGCTCTTTGTGGTGCCAGACTATG (SEQ ID NO: 173) | 44 |
|  | Ta_5D | GTGATAATTATCTACGCTGTGGTTGTGATAATTATCTACGCTGTGGTT (SEQ ID NO: 174) | 48 |
|  | Ta_6D | GCTGCGAATTTAACTATGGGGCTGCGAATTTAACTATGGG (SEQ ID NO: 175) | 40 |
| *Typhula ishikariensis* | Ti_2D | CTACGCTGTTGGTCTTGTGAACTACGCTGTTGGTCTTGTGAA (SEQ ID NO: 176) | 42 |
|  | Ti_3D | GGTCTTGTGAAGCACTTTATTGTGGTCTTGTGAAGCACTTTATTGT (SEQ ID NO: 177) | 46 |
|  | Ti_4D | GTTACGAGGTTCTGCTTCTAATCGTTACGAGGTTCTGCTTCTAATC (SEQ ID NO: 178) | 46 |
|  | Ti_5D | TTCTAATCGTCCTTTACTGCTTCTAATCGTCCTTTACTGC (SEQ ID NO: 179) | 40 |
| *Gaeumannomyces graminis* | Gg_1D | CTGTTGCTTCGGCGGACGATGGCTGTTGCTTCGGCGGACGATGG (SEQ ID NO: 180) | 44 |
|  | Gg_2D | GACGCCGCCGGAGGTTACAAACCGACGCCGCCGGAGGTTACAAACC (SEQ ID NO: 181) | 46 |
|  | Gg_3D | GGACGCCGCCGGAGGTTACAGGACGCCGCCGGAGGTTACA (SEQ ID NO: 182) | 40 |
|  | Gg_4D | CCGCCCGGCGGTCGGGGCCCCACCGCCCGGCGGTCGGGGCCCCA (SEQ ID NO: 183) | 42 |

TABLE 7-continued

Additional dimeric oligonucleotide probes

| Pathogen (Probe Target) | Probe Name | Probe Sequence | Probe Length |
|---|---|---|---|
| Magnaporthe grisea | Mg_1D | CAACCCTCAAGCCCCGGCTTGGTCAACCCTCAAGCCCCGGCTTGGT (SEQ ID NO: 184) | 46 |
|  | Mg_2D | GCATCTCTGAGCCTAAAAGACAAGCATCTCTGAGCCTAAAAGACAA (SEQ ID NO: 185) | 46 |
|  |  |  | 46 |
|  | Mg_5D | GAACCCTCGCTCGGCCCGTCACCGAACCCTCGCTCGGCCCGTCACC (SEQ ID NO: 186) | 46 |
| Magnaporthe oryzae | Mo_1D | GCCTCGGCTTGGTGTTGGGGCGCCTCGGCTTGGTGTTGGGGC (SEQ ID NO: 187) | 42 |
|  | Mo_5D | CACGCCCGCCGGAGGTTCAAAACTCACGCCCGCCGGAGGTTCAAAACT (SEQ ID NO: 188) | 48 |
|  | Mo_6D | CGCCGGAGGTTCAAAACTCTTATTCGCCGGAGGTTCAAAACTCTTATT (SEQ ID NO: 189) | 40 |
|  | Mo_10D | GTGCTCCAGCCGCTAAACCCCAATTCGTGCTCCAGCCGCTAAACCCCAATTC (SEQ ID NO: 190) | 50 |
| Magnaporyhe poae | Mp_1D | CGCCGCCGGAGGTTCAAAACCCGCCGCCGGAGGTTCAAAACC (SEQ ID NO: 191) | 42 |
|  | Mp_2D | CCGCCGGAGGTTCAAAACCCTCCGCCGGAGGTTCAAAACCCT (SEQ ID NO: 192) | 42 |
|  | Mp_3D | AACGCGCCCTCGCTCGGCGGCAACGCGCCCTCGCTCGGCGGC (SEQ ID NO: 193) | 42 |
|  |  |  | 42 |
| Gaeumannomyces incrustans | Gi_1D | GCTCCGAGCGCAGTAGCACGCGCTCCGAGCGCAGTAGCACGC (SEQ ID NO: 194) | 42 |
|  | Gi_2D | GGTTGGCGCCGGTGCCCAGATGGGTTGGCGCCGGTGCCCAGATG (SEQ ID NO: 195) | 44 |
|  | Gi_3D | GTCGCCGCCGGAGGTTCGAAACCGTCGCCGCCGGAGGTTCGAAACC (SEQ ID NO: 196) | 46 |
|  | Gi_4D | CCGCCGGAGGTTCGAAACCCTCCGCCGGAGGTTCGAAACCCT (SEQ ID NO: 197) | 42 |
| Magnaporthe rhizophila | Mr_1D | TTCGAAACCCTGAATTCTAGTGTTCGAAACCCTGAATTCTAGTG (SEQ ID NO: 198) | 44 |
|  | Mr_2D | GAGGTCGCCGCCGGAGGTTCGAAGAGGTCGCCGCCGGAGGTTCGAA (SEQ ID NO: 200) | 46 |
|  | Mr_3D | GCCTGGAGGTCGCCGCCGGAGGTTCGCCTGGAGGTCGCCGCCGGAGGTTC (SEQ ID NO: 201) | 50 |
|  | Mr_4D | CCAGATGGGCCTGGAGGTCGCCGCCCAGATGGGCCTGGAGGTCGCCGC (SEQ ID NO: 202) | 48 |
| Magnaporthe salvinii | Ms_1D | AAGTACATCGGCGGACCCGCTGGGAAGTACATCGGCGGACCCGCTGGG (SEQ ID NO: 203) | 48 |
|  | Ms_2D | GGCGGACCCGCTGGGGCCCTGAGGGCGGACCCGCTGGGGCCCTGAG (SEQ ID NO: 204) | 46 |
|  | Ms_3D | CGCCTCGCTCGGTGGATCCCCGGAGGCGCCTCGCTCGGTGGATCCCCGGAGG (SEQ ID NO: 205) | 52 |
|  | Ms_4D | CCGGAGGGCATTCCAGCCGCTAAACCGGAGGGCATTCCAGCCGCTAAA (SEQ ID NO: 206) | 48 |
| Microdochium bolleyi | Mb_1D | CTGGAAACAGTGCTGCCACCGGTGGACTGGAAACAGTGCTGCCACCGGTGGA (SEQ ID NO: 207) | 46 |
|  | Mb_4D | AAGCCGGCCAGACGACAGCCATAAAAGCCGGCCAGACGACAGCCATAA (SEQ ID NO: 208) | 48 |
|  | Mb_5D | GCCAGACGACAGCCATAAACCGCCAGACGACAGCCATAAACC (SEQ ID NO: 209) | 42 |
|  | Mb_6D | CTGGAAACAGTGCTGCCACCGGTCTGGAAACAGTGCTGCCACCGGT (SEQ ID NO: 210) | 46 |
| Microdochium nivale | Mn_2D | GGTGGATGGTGCTGTCTCTCGGGTGGATGGTGCTGTCTCTCG (SEQ ID NO: 211) | 42 |
|  | Mn_4D | TGGACTACCTAAACTCTGTTATGGACTACCTAAACTCTGTTA (SEQ ID NO: 212) | 42 |
|  | Mn_5D | GTCAATCTGAATCAAACTAAGGTCAATCTGAATCAAACTAAG (SEQ ID NO: 213) | 42 |
|  | Mn_9D | CGGAGTCGGTTCGTGCTCTGACGGAGTCGGTTCGTGCTCTGA (SEQ ID NO: 214) | 42 |

TABLE 7-continued

Additional dimeric oligonucleotide probes

| Pathogen (Probe Target) | Probe Name | Probe Sequence | Probe Length |
|---|---|---|---|
| Gleocercospora sorghi | Gs_1D | CTCGGTGGTTAGTACTCTCTCTCGCTCGGTGGTTAGTACTCTCTCTCG (SEQ ID NO: 215) | 48 |
|  | Gs_2D | CGGTGGTTAGTGCTCTCTCTCGGCGGTGGTTAGTGCTCTCTCTCGG (SEQ ID NO: 216) | 46 |
|  | Gs_4D | TCTCTCTCGGGAGGGTGCTGCCTCTCTCTCGGGAGGGTGCTGCC (SEQ ID NO: 217) | 44 |
|  | Gs_6D | GTAATTACTTATCTCGCTTCTTGTAATTACTTATCTCGCTTCTT (SEQ ID NO: 218) | 44 |
| Laetisaria fuciformis | Lf_1D | CCTTTGGGTGTCCGAGTTGTATTCCTTTGGGTGTCCGAGTTGTATT (SEQ ID NO: 219) | 46 |
|  | Lf_2D | TTTCCGCGCTGGACTGTGTAAATTTCCGCGCTGGACTGTGTAAA (SEQ ID NO: 220) | 44 |
|  | Lf_3D | CGCGTTGTATGAGACTCAGCCTCGCGTTGTATGAGACTCAGCCT (SEQ ID NO: 221) | 44 |
|  | Lf_5D | GGCATCCTTTGGGTGTCCGAGTTGGGCATCCTTTGGGTGTCCGAGTTG (SEQ ID NO: 222) | 48 |
| Leptosphaeria korrae | Lk_1D | TAAAGCAATTGGCAGCCTATATCTTAAAGCAATTGGCAGCCTATATCT (SEQ ID NO: 223) | 48 |
|  | Lk_2D | AGCACAAACTGCATGGGCGGAGCACAAACTGCATGGGCGG (SEQ ID NO: 224) | 40 |
|  | Lk_3D | CCCATTGAACCTATTTATTTTCCCATTGAACCTATTTATTTT (SEQ ID NO: 225) | 42 |
|  | Lk_6D | AGCAATTGGCAGCCTATATCTGGAGCAATTGGCAGCCTATATCTGG (SEQ ID NO: 226) | 46 |
| Ophiosphaerella herpotricha | Oh_1D | TCTTACTGCCAGTTATATAGGCACTCTTACTGCCAGTTATATAGGCAC (SEQ ID NO: 227) | 48 |
|  | Oh_2D | GTGTAGAACAAACTACGCAGACGTGTAGAACAAACTACGCAGAC (SEQ ID NO: 228) | 44 |
|  | Oh_3D | CCAATAAGCCTTTTTATCACCCAATAAGCCTTTTTATCAC (SEQ ID NO: 229) | 40 |
|  | Oh_4D | TCTACTCCACTGCGTTTGGACTCGTCTACTCCACTGCGTTTGGACTCG (SEQ ID NO: 230) | 48 |
| Ophiosphaerella agrostis | Oa_1D | AGAACATAGGCCCCAAGCTGTAGCAGAACATAGGCCCCAAGCTGTAGC (SEQ ID NO: 231) | 48 |
|  | Oa_4D | AAGGCCTCTTCTATTACCCTTGTAAGGCCTCTTCTATTACCCTTGT (SEQ ID NO: 232) | 46 |
|  | Oa_5D | ATCATTACATTAGAACATAGGCCATCATTACATTAGAACATAGGCC (SEQ ID NO: 233) | 46 |
|  | Oa_11D | GGTGTTTTGTCCTCTCCATTGCGGGTGTTTTGTCCTCTCCATTGCG (SEQ ID NO: 234) | 46 |
| Limonomyces roseipellis | Lr_1D | ATATCAATAACACAAACTAACAAGATATCAATAACACAAACTAACAAG (SEQ ID NO: 235) | 48 |
|  | Lr_2D | CTGGCATCCTCCGGGTGTCCGAGTCTGGCATCCTCCGGGTGTCCGAGT (SEQ ID NO: 236) | 48 |
|  | Lr_3D | CTTGTTAGTTTGTGTTATTGATATCTTGTTAGTTTGTGTTATTGATAT (SEQ ID NO: 237) | 48 |
|  | Lr_4D | ACTCGGACACCCGGAGGATGCCAGACTCGGACACCCGGAGGATGCCAG (SEQ ID NO: 238) | 48 |
| Acidovorax avenae | Aa_1D | ATAAAGGGAGGTCATGACGGTATAAAGGGAGGTCATGACGGT (SEQ ID NO: 239) | 42 |
|  | Aa_2D | CTAATAAAGGGAGGTCATGACGCTAATAAAGGGAGGTCATGACG (SEQ ID NO: 240) | 44 |
|  | Aa_3D | CGTCATGACCTCCCTTTATTAGCGTCATGACCTCCCTTTATTAG (SEQ ID NO: 241) | 44 |
|  | Aa_4D | ACCGTCATGACCTCCCTTTATACCGTCATGACCTCCCTTTAT (SEQ ID NO: 242) | 42 |
| Xanthomonas translucens pv. poae | Xt-p_1D | AGTGAAATGCGTAAGATCGGGAGGAAGTGAAATGCGTAAGATCGGGAGGA (SEQ ID NO: 243) | 50 |
|  | Xt-p_2D | CACGGAACTTTCCAGAGATGGATTGCACGGAACTTTCCAGAGATGGATTG (SEQ ID NO: 244) | 50 |
|  | Xt-p_3D | CACAGTGGTAGCAATACCATGGGTGCACAGTGGTAGCAATACCATGGGTG (SEQ ID NO: 245) | 50 |
|  | Xt-p_4D | CACAGTGGTAGCAATACCATGCACAGTGGTAGCAATACCATG (SEQ ID NO: 246) | 42 |

TABLE 7-continued

Additional dimeric oligonucleotide probes

| Pathogen (Probe Target) | Probe Name | Probe Sequence | Probe Length |
|---|---|---|---|
| *Curvularia trifolii* | ct_1 | GGGCGTCTTGTCTTTTGGCTCTGGGCGTCTTGTCTTTTGGCTCT (SEQ ID NO: 247) | 44 |
| | ct_2 | GGCTCTTTGCCCAAAGACTCGGCTCTTTGCCCAAAGACTC (SEQ ID NO: 248) | 40 |
| | ct_3 | CGCCAGGACCACACCATAAACCTCGCCAGGACCACACCATAAACCT (SEQ ID NO: 249) | 46 |
| | ct_4 | GCCGCCAGGACCACACCATAAGCCGCCAGGACCACACCATAA (SEQ ID NO: 250) | 42 |
| *Trichoderma virens* | tv_1 | CGTTACCAAACTGTTGCCTCGGCCGTTACCAAACTGTTGCCTCGGC (SEQ ID NO: 251) | 46 |
| | tv_4 | CAACCCTCGAACCCCTCCGGGCAACCCTCGAACCCCTCCGGG (SEQ ID NO: 252) | 42 |
| | tv_5 | GTATTCTGGCGGGCATGCCTGTCCGTATTCTGGCGGGCATGCCTGTCC (SEQ ID NO: 253) | 48 |
| *Urocystis agropyri* | Ua_1 | GATCTGTATCCGCCCCCGACCCGATCTGTATCCGCCCCCGACCC (SEQ ID NO: 254) | 44 |
| | Ua_3 | GTATCCGCCCCCGACCCTTCGATCGTATCCGCCCCCGACCCTTCGATC (SEQ ID NO: 255) | 48 |
| | Ua_4 | GAGGGTAGCGCCGTTTCATGGTCGGAGGGTAGCGCCGTTTCATGGTCG (SEQ ID NO: 256) | 48 |
| | Ua_5 | CTAATCTAGGAGTGGCATCGAACTAATCTAGGAGTGGCATCGAA (SEQ ID NO: 257) | 44 |
| *Ustilago striiformis* | Us_1 | CGCCCATATCGAGTTTTGCCTCGGCGCCCATATCGAGTTTTGCCTCGG (SEQ ID NO: 258) | 48 |
| | Us_2 | TTACAATGAAATCGACTGGTAATGCTTACAATGAAATCGACTGGTAATGC (SEQ ID NO: 259) | 50 |
| | Us_3 | ACAATGAAATCGACTGGTAATGCACAATGAAATCGACTGGTAATGC (SEQ ID NO: 260) | 46 |
| *Lycoperdon* spp | Ly_1 | GCACACTTGTCTTGACTTTATTCGCACACTTGTCTTGACTTTATTC (SEQ ID NO: 261) | 46 |
| | Ly_4 | GGAGCATGTGCACACTTGTCTTGGAGCATGTGCACACTTGTCTT (SEQ ID NO: 262) | 44 |
| | Ly_5 | CGAGTTGTGATGGGGCTTGGATCCGAGTTGTGATGGGGCTTGGATC (SEQ ID NO: 263) | 46 |
| *Bovista* | Bov_1 | TCCGGATGTGAGGAATTGCTGAGTTCCGGATGTGAGGAATTGCTGAGT (SEQ ID NO: 264) | 48 |
| | Bov_2 | TACCTCTCCTTCAAGTACTATGTTACCTCTCCTTCAAGTACTATGT (SEQ ID NO: 265) | 46 |
| | Bov_4 | ATTAAAATTCTCAACCCCTCTAGCTTTATTAAAATTCTCAACCCCTCTAGCTTT (SEQ ID NO: 266) | 52 |
| | Bov_6 | AAATTCTCAACCCCTCTAGCTTAAATTCTCAACCCCTCTAGCTT (SEQ ID NO: 267) | 44 |
| *Agaricus* | Ag_1 | TGGACTTCATTTTCATCCACCTGTGGACTTCATTTTCATCCACCTG (SEQ ID NO: 268) | 46 |
| | Ag_6 | TCTTTTTCCTGTTAGAGTCTATGTTCTTTTTCCTGTTAGAGTCTATGT (SEQ ID NO: 269) | 48 |
| | Ag_7 | TTGTAGTCTTTTTCAGGTATTGTTGTAGTCTTTTTCAGGTATTG (SEQ ID NO: 270) | 44 |
| | Ag_8 | GTTGTAAAGGAGCTTGGATTGTGTTGTAAAGGAGCTTGGATTGT (SEQ ID NO: 271) | 48 |
| *Marasmius* | Mar_1 | TTGGTATTCCGAGAGGCATGCCTGTTGGTATTCCGAGAGGCATGCCTG (SEQ ID NO: 272) | 48 |
| | Mar_2 | TTGCGCCTCTTGGTATTCCGAGAGGTTGCGCCTCTTGGTATTCCGAGAGG (SEQ ID NO: 273) | 50 |
| *Lepiota* | Le_1 | CATGTAGTATGTTGCCAGAATGCATGTAGTATGTTGCCAGAATG (SEQ ID NO: 274) | 44 |
| | Le_2 | ACCATGTAGTATGTTGCCAGAATGACCATGTAGTATGTTGCCAGAATG (SEQ ID NO: 275) | 48 |
| | Le_3 | TATCACAAACCATGTAGTATGTTTATCACAAACCATGTAGTATGTT (SEQ ID NO: 276) | 46 |

TABLE 7-continued

Additional dimeric oligonucleotide probes

| Pathogen (Probe Target) | Probe Name | Probe Sequence | Probe Length |
|---|---|---|---|
| *Athelia rolfsii* | At_2 | ACATAGAACGATCTCATATTGAAACATAGAACGATCTCATATTGAA (SEQ ID NO: 277) | 46 |
|  | At_3 | ACTCTTATTGTATGTTACATAGAACACTCTTATTGTATGTTACATAGAAC (SEQ ID NO: 278) | 50 |
|  | At_6 | AGAGTCATTAAATTCTCAACCTTAGAGTCATTAAATTCTCAACCTT (SEQ ID NO: 279) | 46 |
|  | At_7 | CAAGGCTTGGATGTGAGAGTTGCTCAAGGCTTGGATGTGAGAGTTGCT (SEQ ID NO: 280) | 48 |
| *Gibberella zeae* | Gz_3 | AAGGGACGGCCCGCCGCAGGAACCCAAGGGACGGCCCGCCGCAGGAACCC (SEQ ID NO: 281) | 50 |
|  | Gz_5 | CTGCACTCCCCAAATACATTGGCGCTGCACTCCCCAAATACATTGGCG (SEQ ID NO: 282) | 48 |
|  | Gz_6 | GCTGCACTCCCCAAATACATTGGCGCTGCACTCCCCAAATACATTGGC (SEQ ID NO: 283) | 48 |
| *Fusarium oxysporum* | Foxy_3 | GGACTCGCGTTAATTCGCGTTCCGGACTCGCGTTAATTCGCGTTCC (SEQ ID NO: 284) | 46 |
|  | Foxy_4 | CGCGTTCCTCAAATTGATTGGCGGTCGCGTTCCTCAAATTGATTGGCGGT (SEQ ID NO: 285) | 50 |
|  | Fo1R | CGTTCCTCAAATTGATTGGCGGTCCGTTCCTCAAATTGATTGGCGGTC (SEQ ID NO: 42) | 48 |
|  | Fox2R | GTTGGGACTCGCGTTAATTCGGTTGGGACTCGCGTTAATTCG (SEQ ID NO: 43) | 42 |
| *Fusarium* spp | Fus_1 | TGTTGCCTCGGCGGATCAGCCCGCTGTTGCCTCGGCGGATCAGCCCGC (SEQ ID NO: 286) | 48 |
|  | Fus_2 | AAATAAATCAAAACTTTCAACAAAAATAAATCAAAACTTTCAACAA (SEQ ID NO: 287) | 46 |
| *Poa annua* (RBCL) | Poa_R_1 | CCTCAGCCTGGAGTTCCCCCGGACCTCAGCCTGGAGTTCCCCCGGA (SEQ ID NO: 288) | 46 |
|  | Poa_R_2 | ACATTGAGCCTGTTGCTGGGGAAGATACATTGAGCCTGTTGCTGGGGAAGAT (SEQ ID NO: 289) | 52 |
|  | Poa_R_4 | CTCAGCCTGGAGTTCCCCCGGACTCAGCCTGGAGTTCCCCCGGA (SEQ ID NO: 290) | 44 |
| *Lolium perenne* (RBCL) | Lp_R_1 | CATATCGAGCCTGTTGCTGGGGAAGACATATCGAGCCTGTTGCTGGGGAAGA (SEQ ID NO: 291) | 52 |
|  | Lp_R_3 | TATCGAGCCTGTTGCTGGGGAAGACATATCGAGCCTGTTGCTGGGGAAGACA (SEQ ID NO: 292) | 52 |
| *Agrostis stolonifera* (RBCL) | As_R_1 | AGTCCTCAACCTGGGGTTCCGCCGAGTCCTCAACCTGGGGTTCCGCCG (SEQ ID NO: 293) | 48 |
|  | As_R_2 | AGTCCTCAACCTGGGGTTCCGCCGGAAGTCCTCAACCTGGGGTTCCGCCGGA (SEQ ID NO: 294) | 52 |
| *Poa annua* (matK) | Poa_m_3 | CGAGTAAGATGGAACATTTTGGCGAGTAAGATGGAACATTTTGG (SEQ ID NO: 295) | 44 |
| *Poa pratensis* (matK) | Pop_m_1 | TGCCAAAATTCGATACCATAGTTCTGCCAAAATTCGATACCATAGTTC (SEQ ID NO: 296) | 48 |
|  | Pop_m_2 | GAATGCCAAAATTCGATACCATAGTGAATGCCAAAATTCGATACCATAGT (SEQ ID NO: 297) | 50 |
| *Agrostis stolonifera* (matK) | As_m_1 | CTATCCATTTTGAAATCTTGGTGCACTATCCATTTTGAAATCTTGGTGCA (SEQ ID NO: 298) | 50 |
|  | As_m_2 | GCAACTCCTTCAATACCGTATCAAGCAACTCCTTCAATACCGTATCAA (SEQ ID NO: 299) | 48 |
|  | As_m_4 | ATTATCTTCTGGAACTTTTCTGGAATTATCTTCTGGAACTTTTCTGGA (SEQ ID NO: 300) | 48 |
|  | As_m_5 | TGCAACTCCTTCAATACCGTATCAATGCAACTCCTTCAATACCGTATCAA (SEQ ID NO: 301) | 50 |
| Positive control | ITS2R | GCTGCGTTCTTCATCGATGCGCTGCGTTCTTCATCGATGC (SEQ ID NO: 48) | 40 |
| Negative control[b] | ITS2_2_IR | GCTGCGTTGATCATCGATGCGCTGCGTTGATCATCGATGC (SEQ ID NO: 57) | 40 |
| Positive control | ITS4R | TCCTCCGCTTATTGATATGCTCCTCCGCTTATTGATATGC (SEQ ID NO: 49) | 40 |
| Negative control | ITS4_2_1R | TCCTCCGTTTATTGATTGCTCCTCCGTTTATTGATTGC (SEQ ID NO: 302) | 40 |
| Negative control | ITS4_2_2R | TCCTCCGTTTATTGAATGCTCCTCCGTTTATTGAATGC (SEQ ID NO: 303) | 40 |

TABLE 7-continued

Additional dimeric oligonucleotide probes

| Pathogen (Probe Target) | Probe Name | Probe Sequence | Probe Length |
|---|---|---|---|
| Negative control | ITS4_2_3R | TCCTCCGTTTATTGGTATGCTCCTCCGTTTATTGGTATGC (SEQ ID NO: 304) | 40 |
| Positive control | matK-390F | CGATCTATTCATTCAATATTTCCGATCTATTCATTCAATATTTC (SEQ ID NO: 305) | 44 |
| Positive control | matK-1326R | TCTAGCACACGAAAGTCGAAGTTCTAGCACACGAAAGTCGAAGT (SEQ ID NO: 306) | 44 |
| Positive control | rbcLaF | ATGTCACCACAAACAGAGACTAAAGCATGTCACCACAAACAGAGACTAAAGC (SEQ ID NO: 307) | 52 |
| Positive control | rbcL-1F | ATGTCACCACAAACAGAAACATGTCACCACAAACAGAAAC (SEQ ID NO: 308) | 40 |

Negative control probe sequences contain nucleotide mismatches as compared to the corresponding positive control probe sequence; these nucleotides are shown in bold.

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. An array that comprises a first plurality of dimeric probes that hybridize to a first target nucleic acid sequence, wherein each of the dimeric probes comprise a first hybridizing nucleic acid sequence and a second hybridizing nucleic acid sequence linked together, wherein the first and second hybridizing nucleic acid sequences are the same and hybridize to the first target nucleic acid sequence, and wherein the first plurality of dimeric probes are selected from SEQ ID NO:4 to SEQ ID NO:9, SEQ ID NO:19 to SEQ ID NO:24, SEQ ID NO:28 to SEQ ID NO:33, SEQ ID NO:42 to SEQ ID NO:45, SEQ ID NO:48 to SEQ ID NO:51, SEQ ID NO:57, SEQ ID NO:58 and SEQ ID NO:73 to SEQ ID NO:301.

2. The array of claim 1, wherein the first and second hybridizing nucleic acid sequences are linked directly together.

3. The array of claim 1, wherein the first and second hybridizing nucleic acid sequences are linked together via a nucleic acid linker sequence.

4. The array of claim 3, wherein the nucleic acid linker sequence is a poly-adenine linker.

5. The array of claim 1, wherein the dimeric probes are about 40-60 nucleotides in length.

6. The array of claim 5, wherein the dimeric probes are about 40-48 nucleotides in length.

7. The array of claim 5, wherein the dimeric probes are about 50-58 nucleotides in length.

8. The array of claim 1, wherein the array further comprises a second plurality of dimeric probes that hybridize to a second target nucleic acid sequence, wherein the second target nucleic acid sequence is from a fungal, viral, or bacterial pathogen.

9. The array of claim 8, wherein the first and second pluralities of dimeric probes hybridize to target nucleic acid sequences in the same pathogen.

10. The array of claim 8, wherein the first and second pluralities of dimeric probes hybridize to target nucleic acid sequences in different pathogens.

11. The array of claim 8, wherein the array further comprises more than two pluralities of dimeric probes that hybridize to different target nucleic acid sequences.

12. The array of claim 11, wherein the more than two pluralities of dimeric probes hybridize to target nucleic acid sequences in the same pathogen.

13. The array of claim 11, wherein the more than two pluralities of dimeric probes hybridize to target nucleic acid sequences in different pathogens.

14. The array of claim 1, wherein the array further comprises pluralities of dimeric probes that specifically hybridize to target nucleic acid sequences in about 50 different pathogens.

15. The array of claim 1, wherein the array further comprises pluralities of dimeric probes that specifically hybridize to target Ob4Anucleic acid sequences in about 100 different pathogens.

16. The array of claim 1, wherein the first target nucleic acid sequence is from *Rhizoctonia solani, Pythium aphanidermatum, Fusarium solani* or *F. oxysporum*.

\* \* \* \* \*